(12) United States Patent
Funahashi et al.

(10) Patent No.: US 7,816,017 B2
(45) Date of Patent: *Oct. 19, 2010

(54) AROMATIC AMINE DERIVATIVE AND ORGANIC ELECTROLUMINESCENCE DEVICE USING THE SAME

(75) Inventors: Masakazu Funahashi, Chiba (JP); Mineyuki Kubota, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 884 days.

This patent is subject to a terminal disclaimer.

(21) Appl. No.: 11/336,855

(22) Filed: Jan. 23, 2006

(65) Prior Publication Data

US 2006/0210830 A1   Sep. 21, 2006

(30) Foreign Application Priority Data

Mar. 15, 2005   (JP) .............................. 2005-073474

(51) Int. Cl.
- *H01L 51/54* (2006.01)
- *H05B 33/14* (2006.01)
- *C09K 11/06* (2006.01)
- *C07C 211/58* (2006.01)

(52) U.S. Cl. ................. 428/690; 428/917; 313/504; 313/506; 564/429; 556/413; 257/40

(58) Field of Classification Search ................. 428/690, 428/917; 564/426–434
See application file for complete search history.

(56) References Cited

U.S. PATENT DOCUMENTS

| 6,743,948 | B1 | 6/2004 | Hosokawa et al. |
| 2004/0191563 | A1 | 9/2004 | Iwakuma et al. |
| 2005/0038296 | A1 | 2/2005 | Hosokawa et al. |
| 2005/0064233 | A1 | 3/2005 | Matsuura et al. |
| 2006/0052641 | A1 | 3/2006 | Funahasi |
| 2006/0152146 | A1* | 7/2006 | Funahashi .................. 313/504 |

FOREIGN PATENT DOCUMENTS

| EP | 0 106 112 A1 | 4/1984 |
| EP | 1561794 A1 | 8/2005 |
| JP | 2001-052868 | 2/2001 |
| JP | 2001-131541 | 5/2001 |
| JP | 2003-040845 | 2/2003 |
| WO | WO 00/39247 A1 | 7/2000 |
| WO | WO 2004/044088 A1 | 5/2004 |

OTHER PUBLICATIONS

U.S. Appl. No. 11/550,519, filed Oct. 18, 2006, Funahashi, et al.
U.S. Appl. No. 11/596,299, filed Nov. 13, 2006, Funahashi.
U.S. Appl. No. 11/575,441, filed Mar. 16, 2007, Funahashi.
U.S. Appl. No. 11/336,857, filed Jan. 23, 2006, Funahashi.
U.S. Appl. No. 11/344,604, filed Feb. 1, 2006, Hosokawa, et al.
U.S. Appl. No. 11/282,697, filed Nov. 21, 2005, Funahashi.

* cited by examiner

*Primary Examiner*—D. L Tarazano
*Assistant Examiner*—Camie S Thompson
(74) *Attorney, Agent, or Firm*—Oblon, Spivak, McClelland, Maier & Neustadt, L.L.P.

(57) ABSTRACT

A aromatic amine derivative having an specific structure having a diphenyl amino group, and two or more of substituent bonding to benzene ring thereof, and in an organic electroluminescence device which comprises at least one organic thin film layer comprising a light emitting layer sandwiched between a pair of electrode consisting of an anode and a cathode, at least one of the organic thin film layer comprises the aromatic amine derivative singly or a component for a mixture thereof. The organic electroluminescence device exhibiting a long lifetime and high current efficiency as well as emitting blue light with high color purity, and also the aromatic amine derivative for realizing the organic EL device are provided.

18 Claims, 4 Drawing Sheets

AROMATIC AMINE DERIVATIVE AND ORGANIC ELECTROLUMINESCENCE DEVICE USING THE SAME

CROSS-REFERENCE TO RELATED APPLICATION

The present application claims priority to Japanese patent application JP 2005-073474, filed on Mar. 15, 2005.

TECHNICAL FIELD

The present invention relates to an aromatic amine derivative and an organic electroluminescence ("electroluminescence" will be occasionally referred to as "EL", hereinafter) device using the aromatic amine derivative, in particular, to an organic electroluminescence device having a long lifetime, exhibiting high current efficiency and emitting a blue light with high color purity, and also to the aromatic amine derivative for realizing the organic EL device.

BACKGROUND ART

Since an organic EL device employing organic materials has been expected as an application for a display device based on a solid light emission having a popular price and a large viewing surface, substantial development have been conducted.

An organic EL device is constructed generally from a light emitting layer and a pair of counter electrodes which sandwiches the layer. A light emission is a phenomenon as follows; when an electric field is applied between the electrodes, electrons are injected from the cathode side and holes are injected from the anode side. Further, the electrons recombine with the holes in the light emitting layer to produce its excitation state, and the energy from the excitation state is released as a light on returning to the ground state. The conventional organic EL devices required a higher driving voltage and had lower luminance and current efficiency in comparison with inorganic light emission diodes. In addition, the devices have not yet been put to practical use due to notable deterioration of properties thereof.

Although current organic EL devices have been improved by inches, longer lifetime as well as higher current efficiency has been desired. For example, the technology employed the individual mono-anthracene compounds as an organic. light emission material has been disclosed (Patent literature 1). However, it has provided with the organic EL devices having for example, only the luminance of 1650 cd/m² at the luminance of 165 mA/cm², and also the current efficiency is extremely low so as to put them in practical use.

Further, the technology employing the individual bisanthracene compounds as an organic light emission material has been disclosed (Patent literature 2). However, it has provided with an organic EL device having the low current efficiency such as 1 to 3 cd/A, therefore further improvement has been required so as to put in practical use.

Meanwhile, the organic EL device with a long lifetime, which employed the distyryl compound added by styryl amine or so forth as an organic light emitting material, has been proposed (Patent literature). However, the device has been required to improve its inadequate lifetime further. In addition, the technology employing the organic light emitting medium layer of the monoanthracene compounds or the bisanthracene compounds, and the distyryl compounds has been disclosed (Patent literature 4). However, it has provided with worsened color purity since the emission spectrum become long wavelength due to the conjugated structure of the styryl compounds.

Further, the devices emitting blue light employed the diaminochrysene derivatives have been disclosed in Patent literature 5. However, the device has been required to improve its inadequate lifetime in spite of its excellent current efficiency.

Patent literature 1: Japanese Patent Application Laid-open No. Heisei 11 (1999)-3782, Patent literature 2: Japanese Patent Application Laid-open No. Heisei 8 (1996)-12600, Patent literature 3: International PCT publication No. WO 094/006157, Patent literature 4: Japanese Patent Application Laid-open No. 2001-284050, Patent literature 5: International PCT publication No. WO 04/044088.

DISCLOSURE OF THE INVENTION

The present invention has been made to overcome the above problems and has an objective of providing an organic electroluminescence device having a long lifetime, exhibiting the high current efficiency and emitting blue light with high color purity, and also providing an aromatic amine derivative for realizing the organic EL device.

As a results of intensive researches and studies to provide with an aromatic amine derivative having the above preferred properties and with an organic EL device employing the derivative, it has been found that the objective can be accomplished by employing the aromatic amino derivative represented by the general formula (1). The derivative contains a diphenyl amino group and two or more of substituents bonded to benzene ring thereof. Such being the case, the present invention has been accomplished on the basis of the foregoing findings and information.

Namely, the present invention is to provide the aromatic amine derivative represented by the following general formula (1).

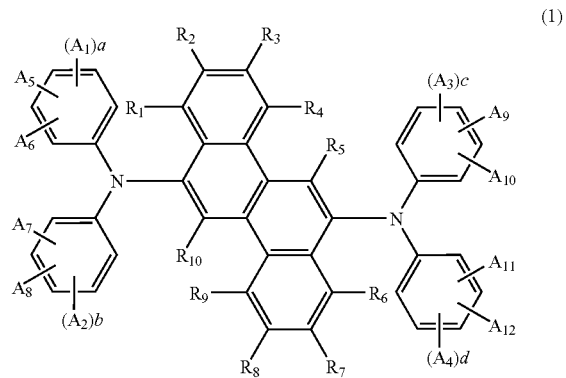

In the general formula (1), $A_1$ to $A_4$ each independently represents a hydrogen atom, a substituted or unsubstituted alkyl group having carbon atoms of 1 to 50, a substituted or unsubstituted aryl group having ring carbon atoms of 5 to 50, a substituted or unsubstituted aralkyl group having ring carbon atoms of 6 to 50, a substituted or unsubstituted cycloalkyl group having ring carbon atoms of 3 to 50, a substituted or unsubstituted alkoxyl group having ring carbon atoms of 1 to 50, a substituted or unsubstituted aryloxy group having ring carbon atoms of 5 to 50, a substituted or unsubstituted arylamino group having ring carbon atoms of 5 to 50, a substituted or unsubstituted alkylamino group having carbon atoms of 1 to 20, a substituted or unsubstituted hetero ring group having ring carbon atoms of 5 to 50 or a halogen atom. a, b, c and d each independently represents an integer of 0 to 3.

When a, b, c and d each is two or more, $A_1$ to $A_4$ are the same with or different from each other.

$A_5$ to $A_{12}$ each independently represents a substituted or unsubstituted alkyl group having carbon atoms of 1 to 50, a substituted or unsubstituted aryl group having ring carbon atoms of 5 to 50, a substituted or unsubstituted aralkyl group having ring carbon atoms of 6 to 50, a substituted or unsubstituted cycloalkyl group having ring carbon atoms of 3 to 50, a substituted or unsubstituted alkoxyl group having ring carbon atoms of 1 to 50, a substituted or unsubstituted aryloxy group having ring carbon atoms of 5 to 50, a substituted or unsubstituted arylamino group having ring carbon atoms of 5 to 50, a substituted or unsubstituted alkylamino group having carbon atoms of 1 to 20, a substituted or unsubstituted hetero ring group having ring carbon atoms of 5 to 50 or a halogen atom. $A_5$ and $A6$, $A_7$ and $A_8$, $A_9$ and $A_{10}$, and $A_{11}$ and $A_{12}$ may respectively bond each other to form a saturated or unsaturated ring.

$R_1$ to $R_{10}$ each independently represents a hydrogen atom, a substituted or unsubstituted alkyl group having carbon atoms of 1 to 20, a substituted or unsubstituted aryl group having ring carbon atoms of 5 to 20, a substituted or unsubstituted aralkyl group having ring carbon atoms of 1 to 20, a substituted or unsubstituted cycloalkyl group having ring carbon atoms of 3 to 20.

Further, the present invention provides an organic EL device comprising at least one of organic thin film layers including a light emitting layer sandwiched between a pair of electrode consisting of an anode and a cathode, wherein a least one of the organic thin film layers contains the aromatic amine derivative singly or as a component for a mixture thereof.

An organic EL device employing an aromatic amine derivative of the present invention exhibits adequate luminance of emitted light at low driving voltage and high current efficiency, and has a long lifetime due to its difficult deterioration during a long time use.

BRIEF DESCRIPTION OF DRAWINGS

FIG. 1 shows $^1$H-NMR spectrum of the amine derivative obtained in Synthesis Example 1.

FIG. 2 shows $^1$H-NMR spectrum of the amine derivative obtained in Synthesis Example 2.

FIG. 3 shows $^1$H-NMR spectrum of the amine derivative obtained in Synthesis Example 3.

FIG. 4 shows $^1$H-NMR spectrum of the amine derivative obtained in Synthesis Example 4.

THE PREFERRED EMBODIMENT TO CARRY OUT THE INVENTION

Figure 1:
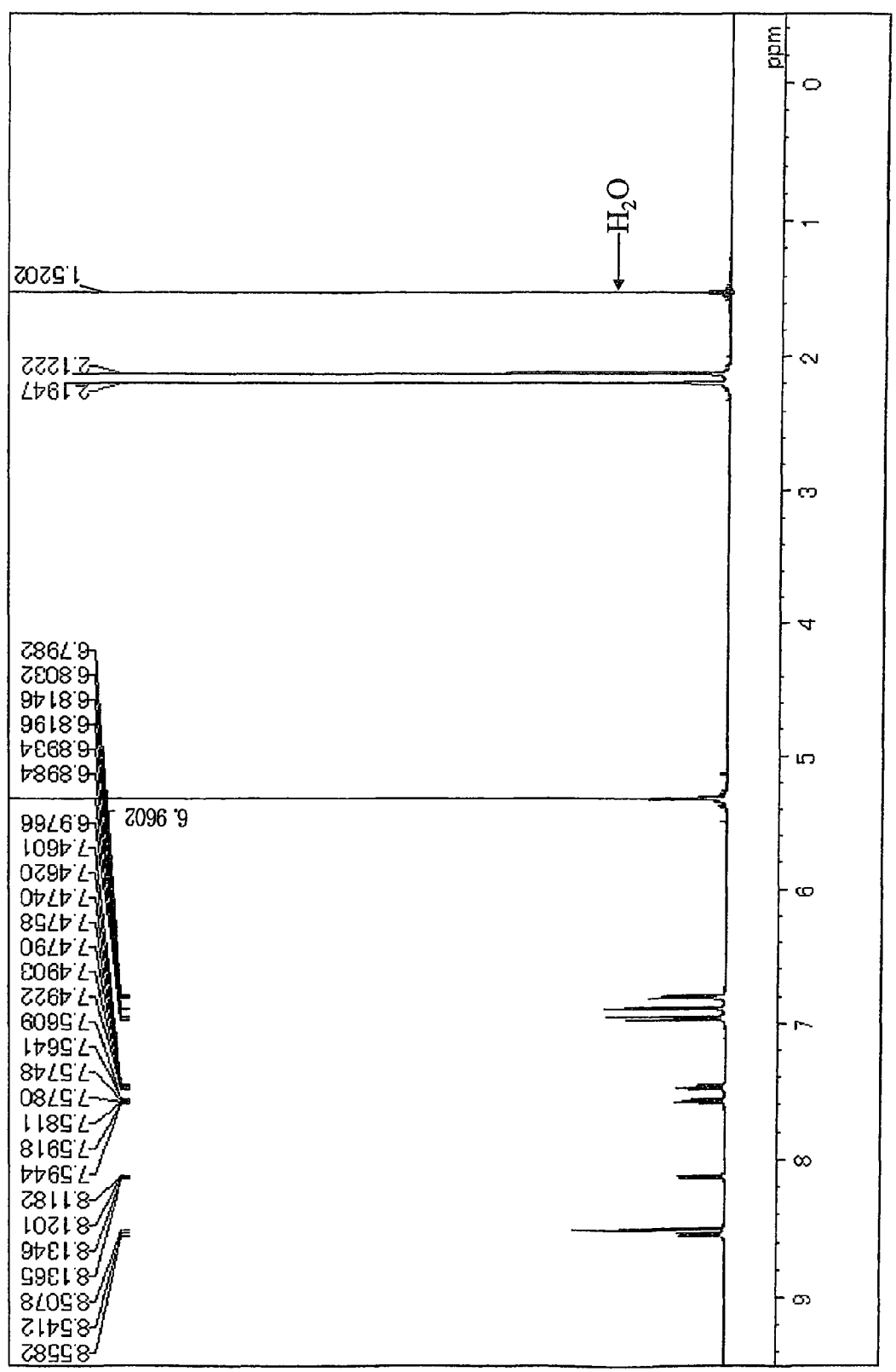
FIG. 1

The aromatic amine derivative of the present invention is represented by the following general formula (1):

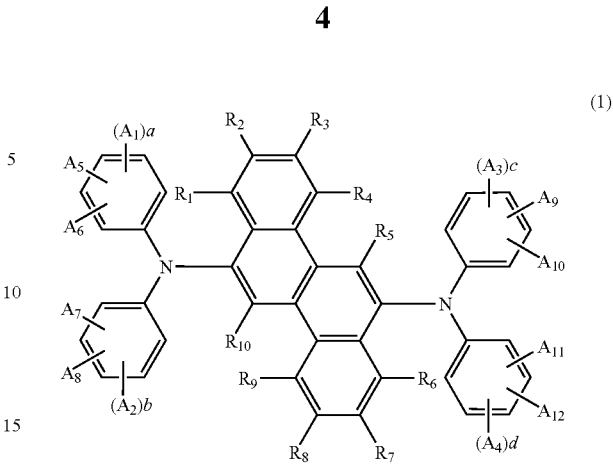

The aromatic amine derivative represented by the general formula (1) is explained as follows;

In the general formula (1), $A_1$ to $A_4$ each independently represents a hydrogen atom, a substituted or unsubstituted alkyl group having carbon atoms of 1 to 50, preferably 1 to 20, a substituted or unsubstituted aryl group having ring carbon atoms of 5 to 50, preferably 5 to 20, a substituted or unsubstituted aralkyl group having ring carbon atoms of 6 to 50, preferably 6 to 20, a substituted or unsubstituted cycloalkyl group having ring carbon atoms of 3 to 50, preferably 5 to 12, a substituted or unsubstituted alkoxyl group having ring carbon atoms of 1 to 50, preferably 1 to 6, a substituted or unsubstituted aryloxy group having ring carbon atoms of 5 to 50, preferably 5 to 18, a substituted or unsubstituted aryl amino group having ring carbon atoms of 5 to 50, preferably 5 to 18, a substituted or unsubstituted alkylamino group having carbon atoms of 1 to 20, preferably 1 to 6, a substituted or unsubstituted hetero ring group having ring carbon atoms of 5 to 50, preferably 5 to 20 or a halogen atom.

$A_5$ to $A_{12}$ each independently represents a substituted or unsubstituted alkyl group having carbon atoms of 1 to 50, preferably 1 to 20, a substituted or unsubstituted aryl group having ring carbon atoms of 5 to 50, preferably 5 to 20, a substituted or unsubstituted aralkyl group having ring carbon atoms of 6 to 50, preferably 6 to 20, a substituted or unsubstituted cycloalkyl group having ring carbon atoms of 3 to 50, preferably 5 to 12, a substituted or unsubstituted alkoxyl group having ring carbon atoms of 1 to 50, preferably 1 to 6, a substituted or unsubstituted aryloxy group having ring carbon atoms of 5 to 50, preferably 5 to 18, a substituted or unsubstituted arylamino group having ring carbon atoms of 5 to 50, preferably 5 to 18, a substituted or unsubstituted alkylamino group having carbon atoms of 1 to 20, preferably 1 to 6, a substituted or unsubstituted hetero ring group having ring carbon atoms of 5 to 50, preferably 5 to 20 or a halogen atom.

An alkyl group for $A_1$ to $A_{12}$ includes, for example, methyl group, ethyl group, propyl group, isopropyl group, butyl group, sec-butyl group, tert-butyl group, pentyl group, hexyl group, heptyl group, octyl group, stearyl group, 2-phenylisopropyl group, trichloromethyl group, trifluoromethyl group, benzyl group, α-phenoxybenzyl group, α,α-dimethylbenzyl group, α,α-methylphenylbenzyl group, α,α-ditrifluoromethylbenzyl group, triphenylmethyl group and α-benzyloxybenzyl group.

An aryl group of $A_1$ to $A_{12}$ includes, for example, phenyl group, 2-methylphenyl group, 3-methylphenyl group, 4-methylphenyl group, 4-ethylphenyl group, biphenyl group, 4-methlbiphenyl group, 4-ethylbiphenyl group, 4-cyclohexylbiphenyl group, terphanyl group, 3,5-dichlorophenyl group, naphthyl group, 5-methylnaphthyl group, anthryl group, pyrenyl group, chrysenyl group, fluroranthenyl group and perylenyl group.

An aralkyl group for $A_1$ to $A_{12}$ includes, for example, benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodeben-5-zyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group and the like.

A cycloalkyl group for $A_1$ to $A_{12}$ includes, for example, cyclopropyl group, cyclobutyl group, cyclipentyl group, cyclohexyl group, cycloheptyl group, cyclooctyl group, cyclononyl group, bicycloheptyl group, bicyclooctyl group, tricycloheptyl group and adamantyl group. Cyclopentyl group, cyclohexyl group, cycloheptyl group, bicycloheptyl group, bicyclooctyl group and adamantyl group are preferable.

An alkoxy group for $A_1$ to $A_{12}$ includes, for example, methoxy group, ethoxy group, propoxy group, isopropoxy group, butoxy group, isobutoxy group, sec-butoxy group, tert-butoxy group, various pentyloxy groups and various hexyloxy groups. An aryloxy group for $A_1$ to $A_{12}$ includes, for example, pheoxy group, tilyloxy group and naphtyloxy group.

An arylamino group for $A_1$ to $A_{12}$ includes, for example, diphenylamino group, ditolylamino group, dinaphthylamino group and naphthylphenylamino group. An alkylamino group for $A_1$ to $A_{12}$ includes, for example, dimethylamino group, diethylamino group and dihexylamino group.

A hetero ring group for A1 to A12 includes a moiety of, for example, imidazole, benzoimidazole, pyrrole, furan, thiophene, benzothophene, oxadiazoline, indoline, carbazol, pyridine, quinoline, isoquinoline, benzoquinone, pyrazine, imidazolidine and piperidine. A halogen atom for A1 to A12 includes, for example, a fluorine atom, a chlorine atom and a bromine atom.

In the general formula (1), a to d each independently represents an integer of 0 to 3, preferably 0 to 1.

When a to d each is two or more, $A_1$ to $A_4$ are the same with or different from each other and also may bond each other to form a saturated or unsaturated ring.

In addition, $A_5$ and $A_6$, $A_7$ and $A_8$, $A_9$ and $A_{10}$, and $A_{11}$ and $A_{12}$ may respectively bond each other to form a saturated or unsaturated ring.

The above ring includes, for example, cycloalkane having carbon atoms of 4 to 12 such as cyclobutane, cyclopentane, cyclohexane adamantane, and norbornane, cycloalkene having carbon atoms of 4 to 12 such as cyclobutene, cyclopentene, cyclohexene, cycloheptene and cyclooctene, cycloalkadiene having carbon atoms of 6 to 12 such as cylohexadiene, cycloheptadiene and cyclooctadiene, an aromatic ring having ring carbon atoms of 6 to 50 such as benzene, naphthalene, phenanthrene, anthracene, pyrene, chrysene and acenaphthylene, and a hetero ring having ring carbon atoms of 5 to 50 such as imidazole, pyrrole, furan, thiophene and pyridine.

In the general formula (1), $R_1$ to $R_{10}$ each independently represents a hydrogen atom, a substituted or unsubstituted alkyl group having carbon atoms of 1 to 20, a substituted or unsubstituted aryl group having carbon atoms of 5 to 20, a substituted or unsubstituted aralkyl group having carbon atoms of 1 to 20 or a substituted or unsubstituted cycloalkyl group having carbon atoms of 3 to 20.

An example for the above each group includes the groups, of which the carbon atom number fits to those of the groups among the groups shown for $A_1$ to $A_{12}$.

A substituent for $A_1$ to $A_{12}$ and $R_1$ to $R_{10}$ above includes a substituted or unsubstituted aryl group having ring carbon atoms of 5 to 50, a substituted or unsubstituted alkyl group having carbon atoms of 1 to 50, a substituted or unsubstituted alkoxy group having carbon atoms of 1 to 50, a substituted or unsubstituted aralkyl group having carbon atoms of 6 to 50, a substituted or unsubstituted aryloxy group having ring carbon atoms of 5 to 50, a substituted or unsubstituted arylthio group having ring carbon atoms of 5 to 50, a substituted or unsubstituted alkoxycarbonyl group having carbon atoms of 1 to 50, an amino group, a halogen atom, a cyano group, a hydroxyl group and carboxyl group.

Among those, an alkyl group having carbon atoms of 1 to 10, a cycloalkyl group having carbon atoms of 5 to 7, a alkoxy group having carbon atom of 1 to 10 and a cycloalkyl group having carbon atoms of 5 to 7 are preferable, and methyl group, ethyl group, n-propyl group, isopropyl group, n-butyl group, sec-butyl group, tert-butyl group, n-pentyl group, n-hexyl group, cyclopentyl group and cyclohexyl group are particularly preferable.

As an aromatic amine derivative of the present invention represented by the general formula (1), a structure represented by the following general formula (2) is preferable; the formula (2) means that $R_1$ to $R_{10}$ are hydrogen atoms in the general formula (1).

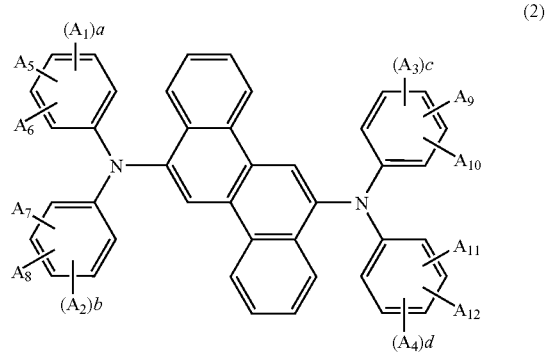

(2)

Further, in the general formulae (1) and (2), it is preferable that A5 to A12 each independently represents a substituted or unsubstituted alkyl group having carbon toms of 1 to 50, and it is particularly preferable that A1 to A12 each independently represents a substituted or unsubstituted alkyl group having carbon atoms of 1 to 50.

The specific examples of the aromatic amine derivatives represented by the general formulae (1) and (2) include the following, but not limited thereto;

D-1
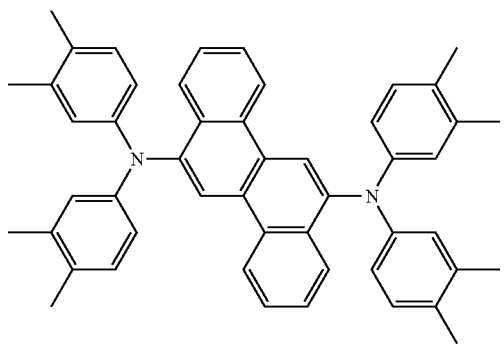
D-2
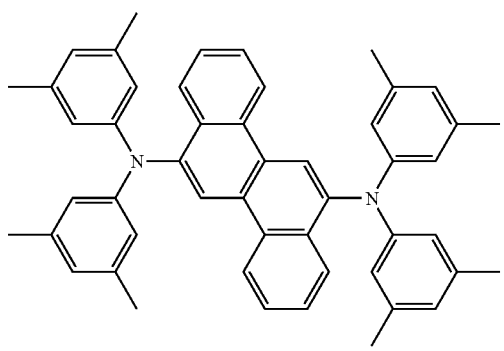
D-3
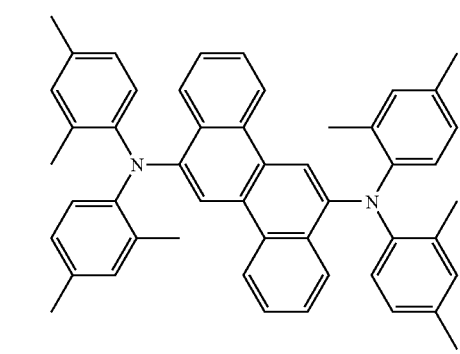
D-4
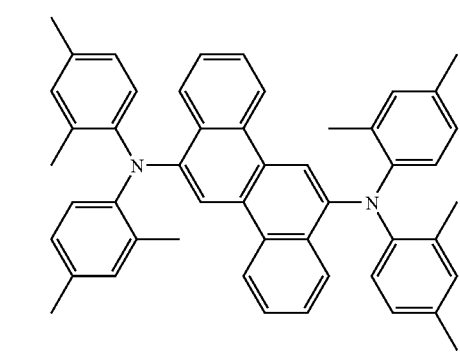
-continued
D-5
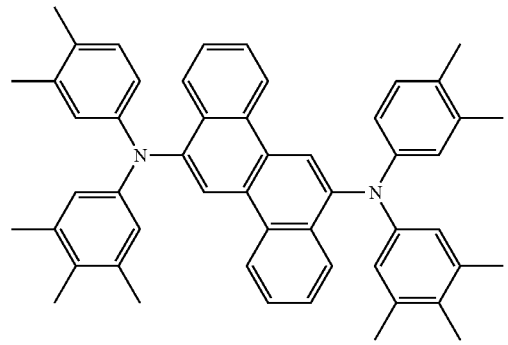
D-6
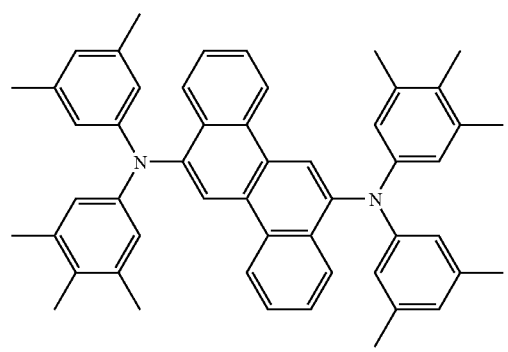
D-7
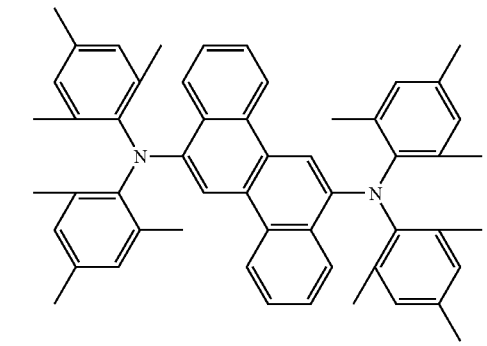
D-8
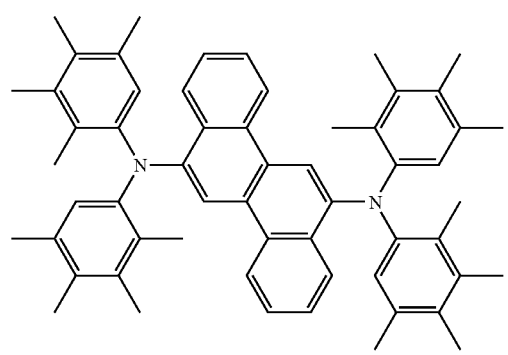

-continued
D-9
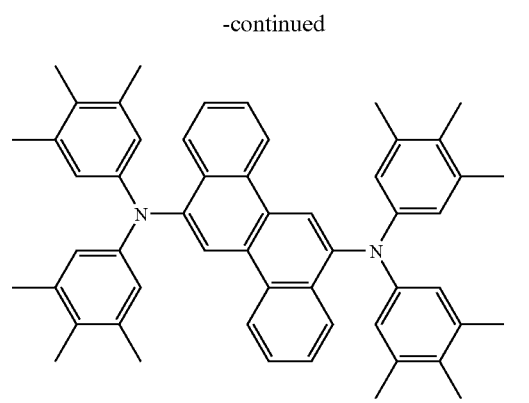
D-10
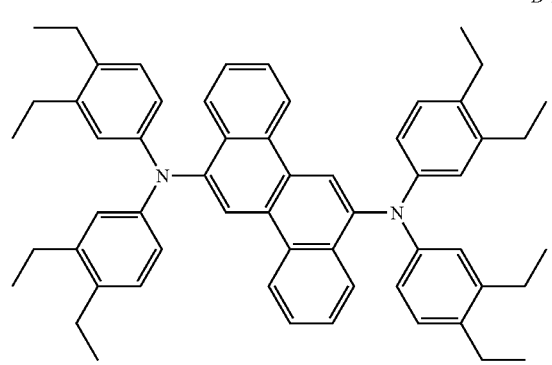
D-11
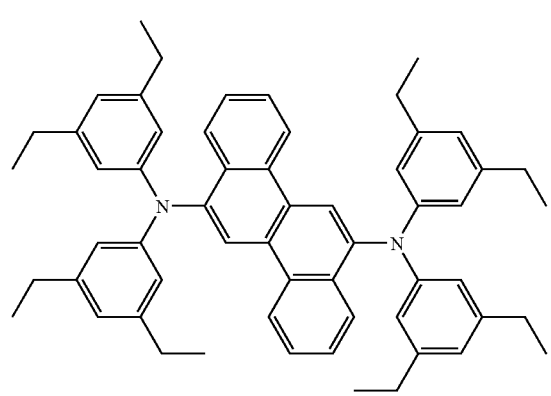
D-12
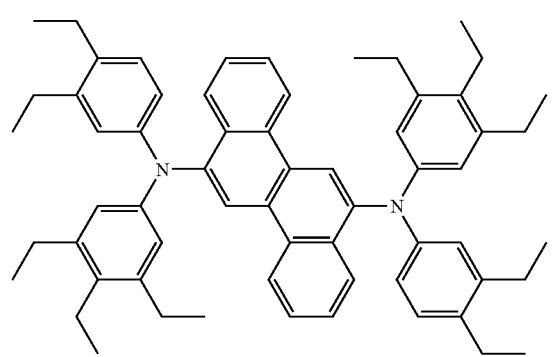
-continued
D-13
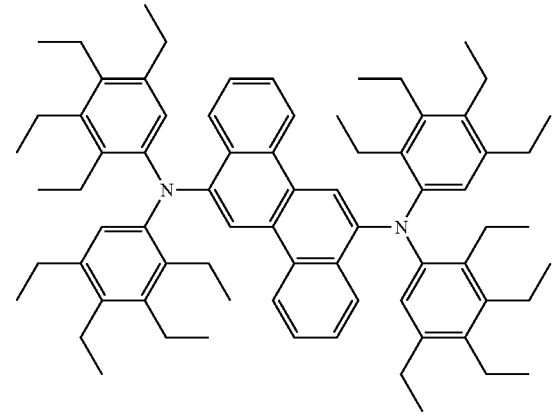
D-14
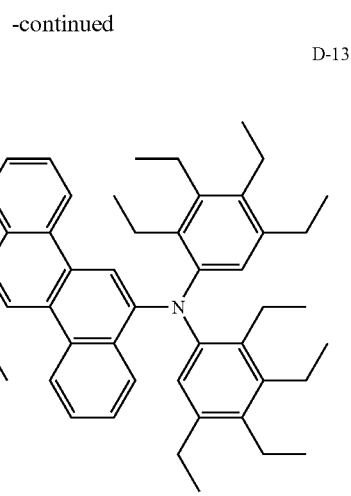
D-15
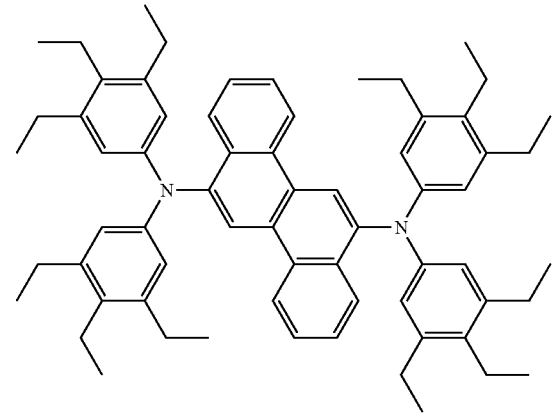

-continued
D-16
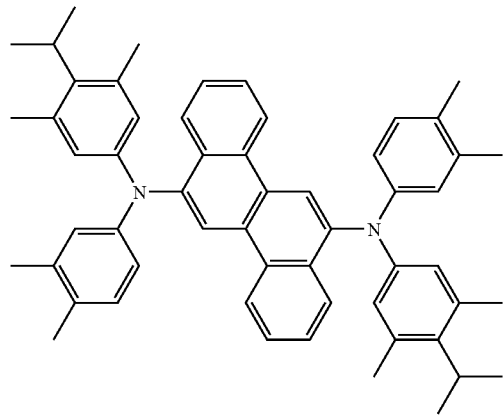
D-17
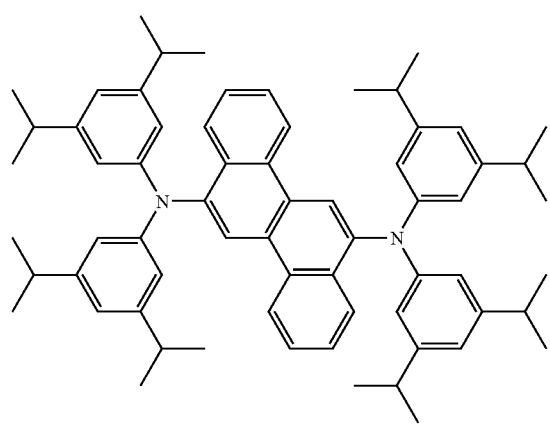
D-18
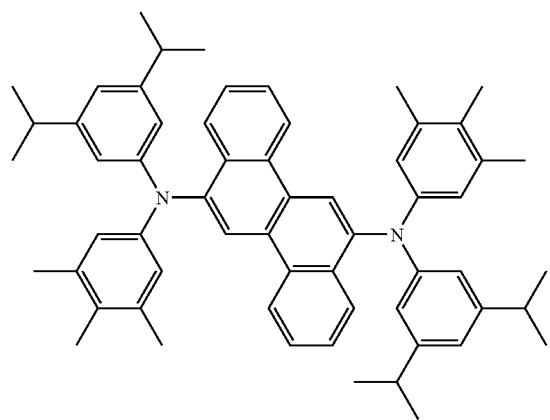
-continued
D-19
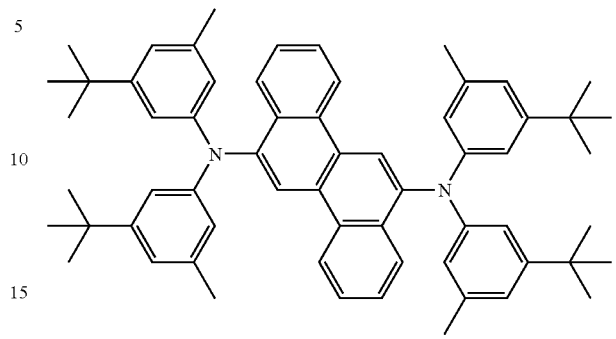
D-20
D-21
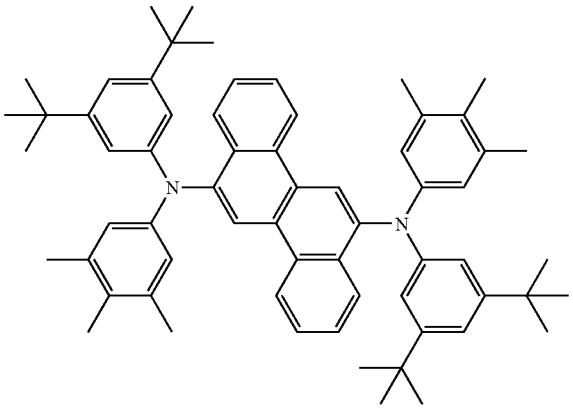

-continued
D-22
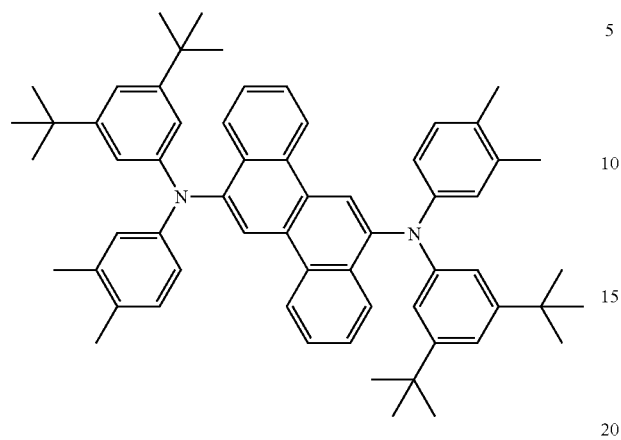
D-23
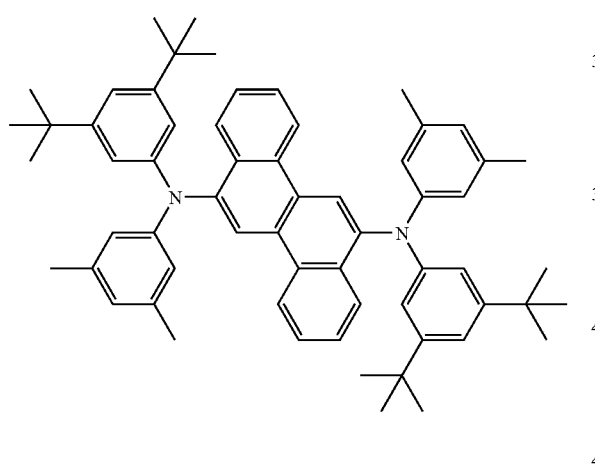
D-24
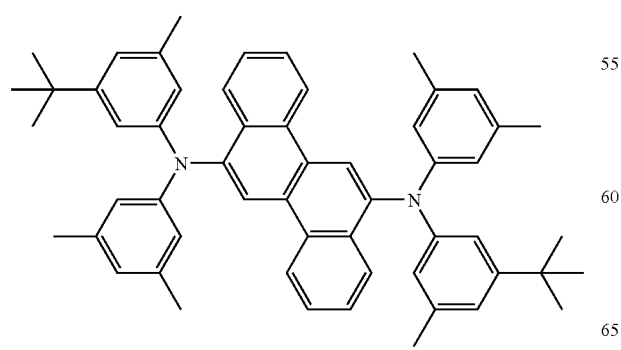
-continued
D-25
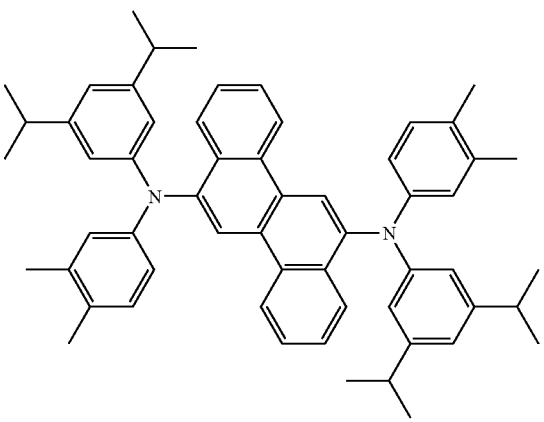
D-26
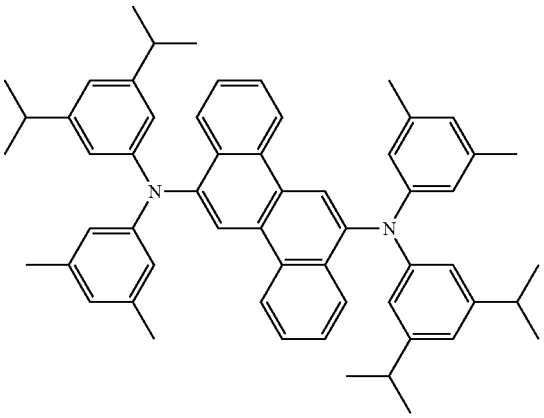
D-27
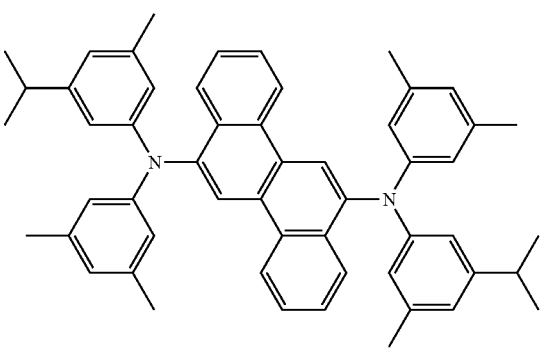

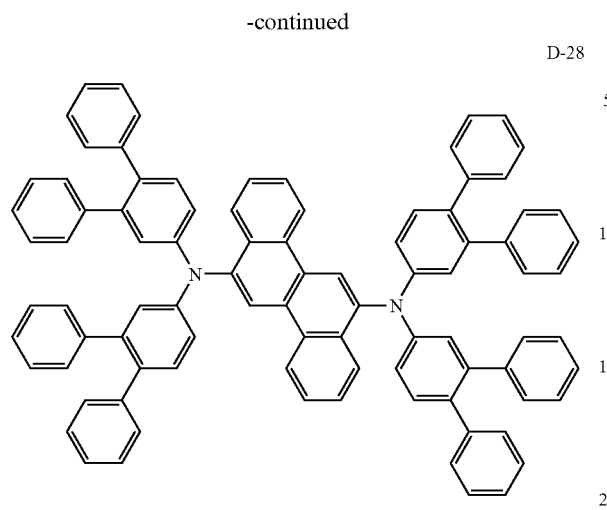
D-28
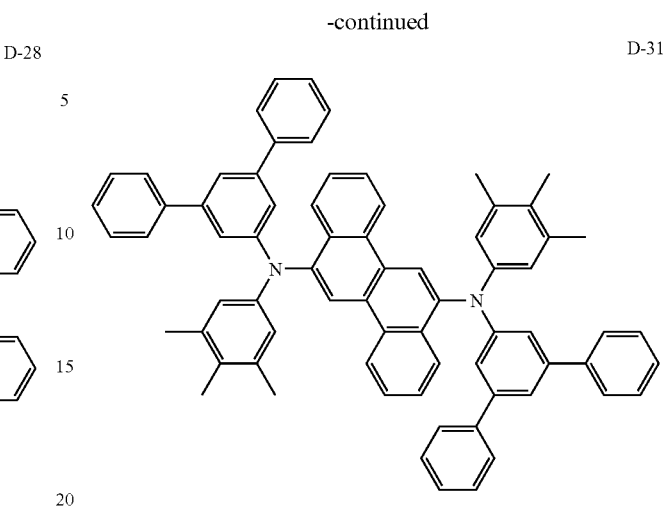
D-31
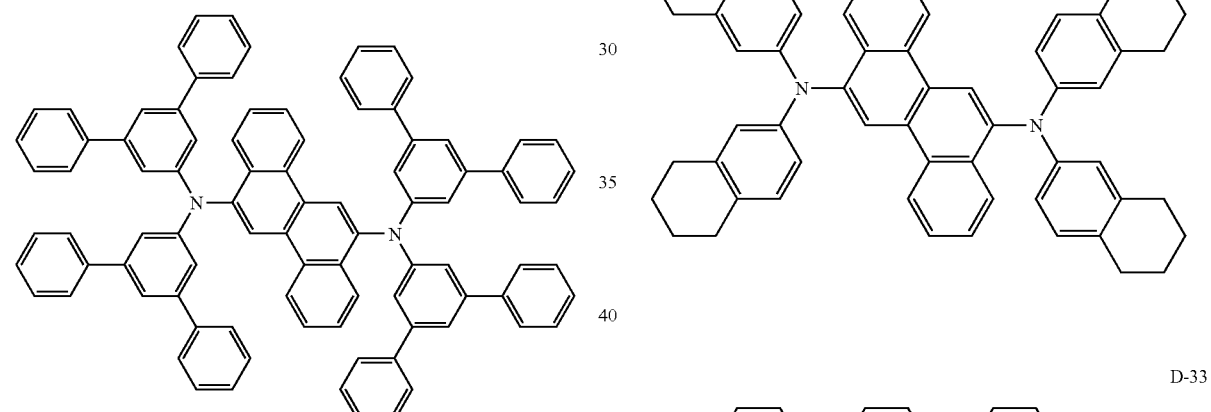
D-29
D-32
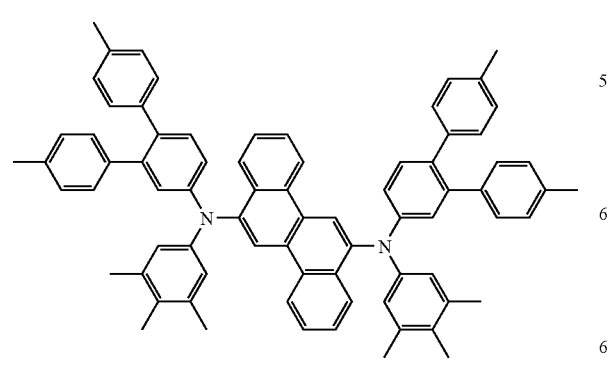
D-30
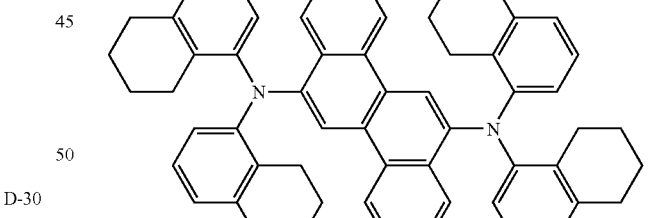
D-33
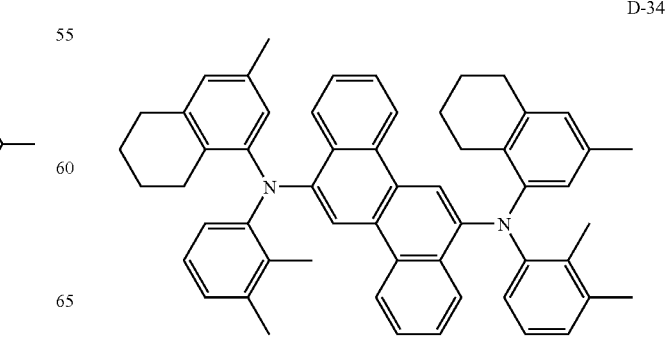
D-34

-continued
D-35
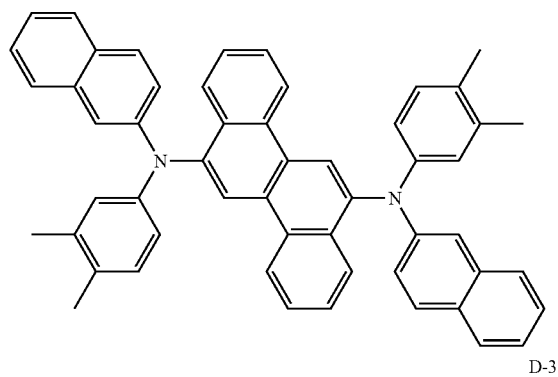
D-36
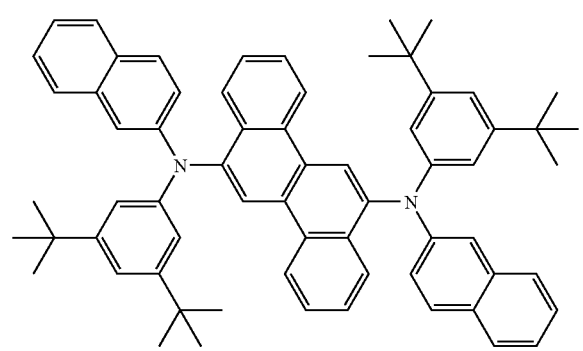
D-37
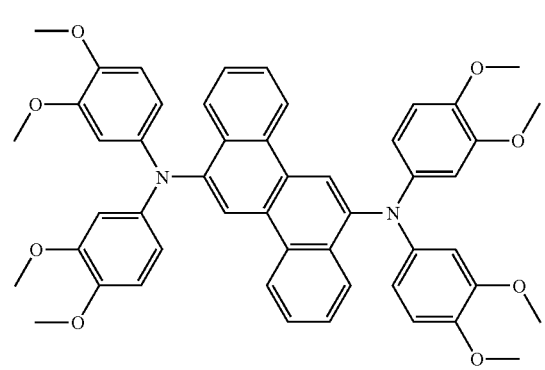
D-38
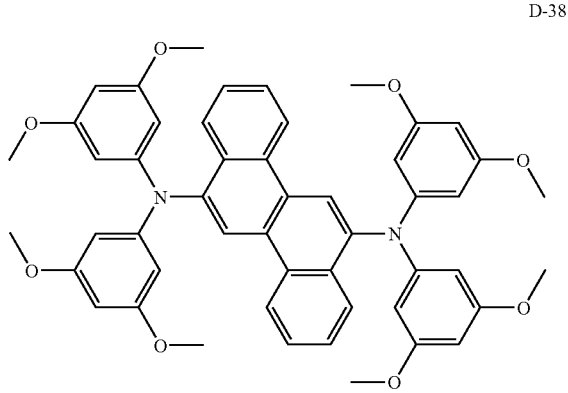
-continued
D-39
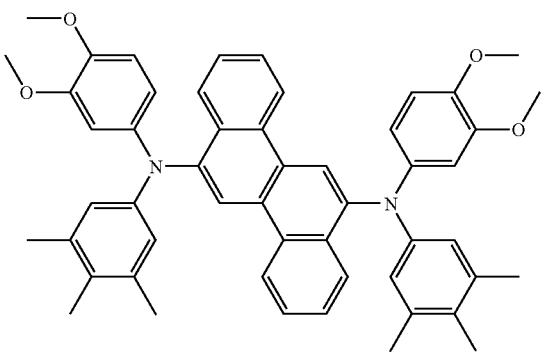
D-40
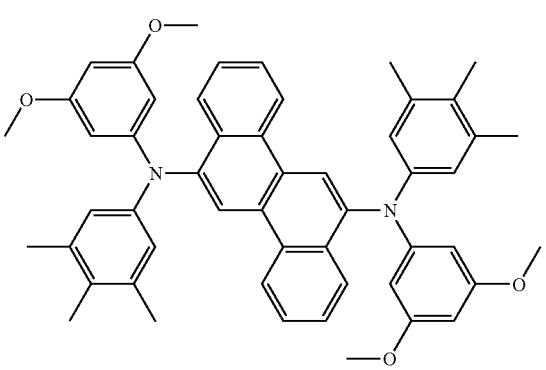
D-41
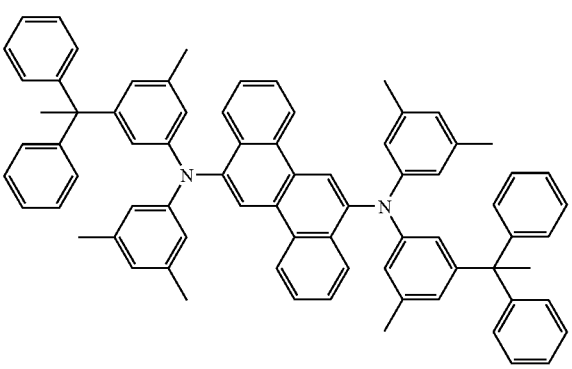
D-42
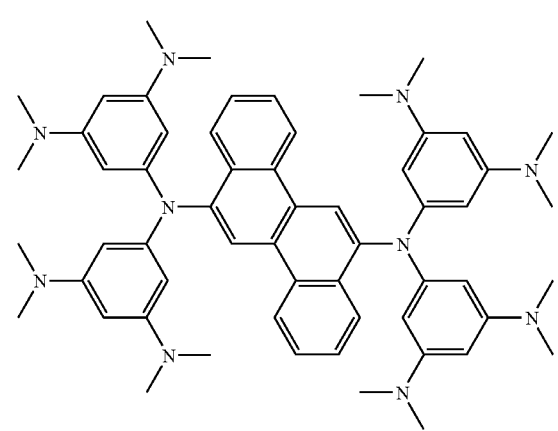

-continued
D-43
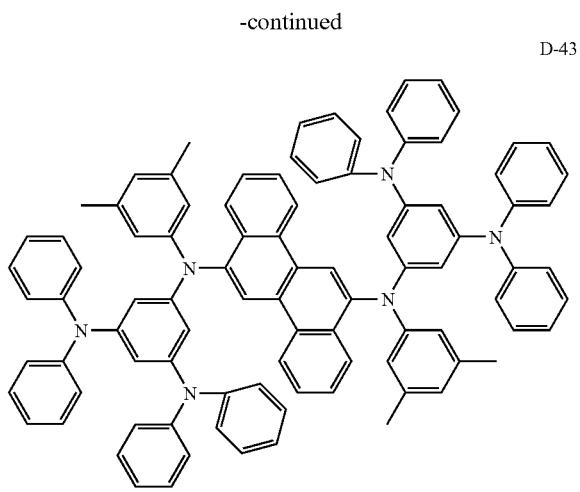
D-44
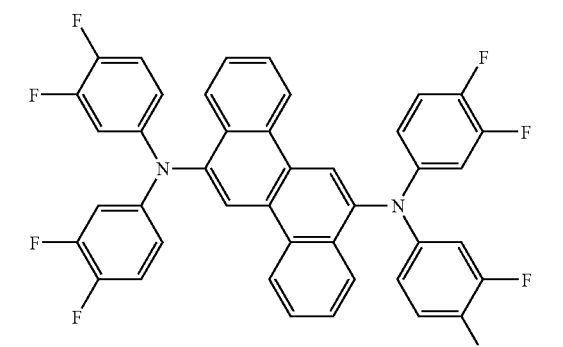
D-45
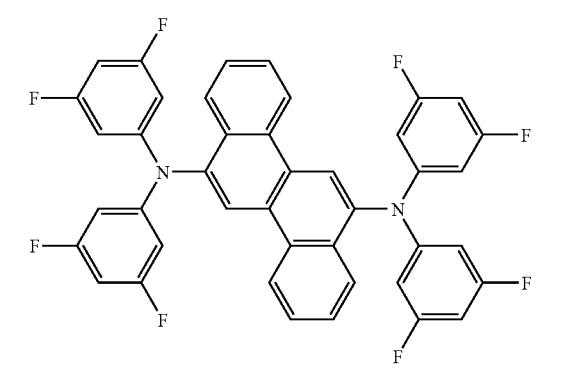
D-46
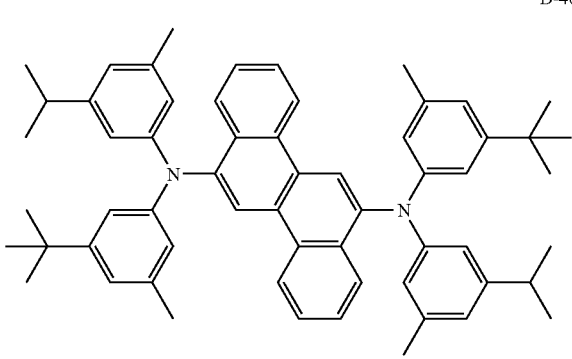
-continued
D-47
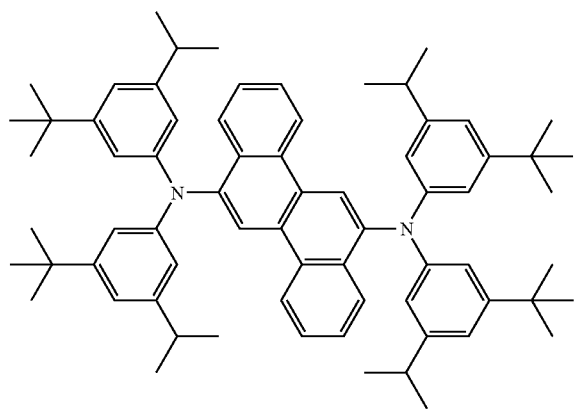
D-48
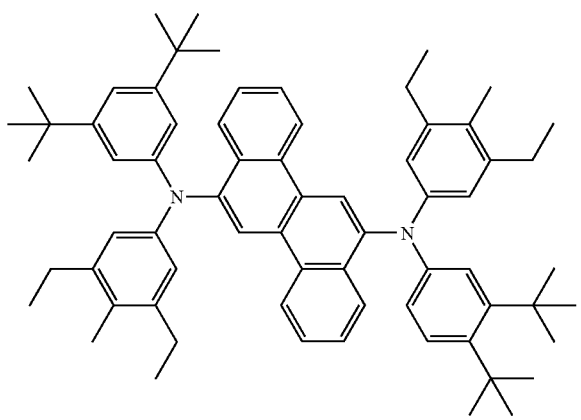
D-49
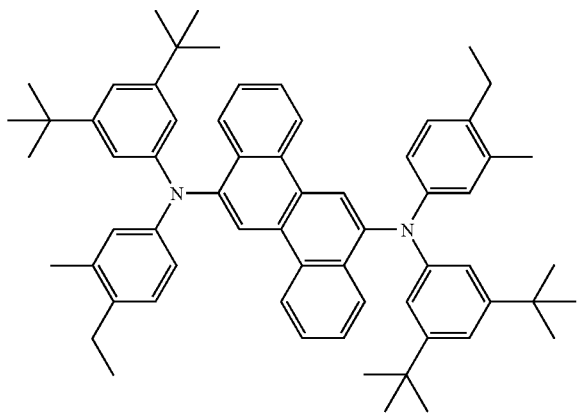

-continued
D-50
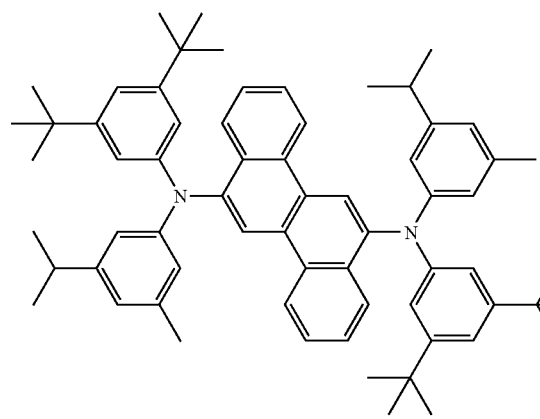
D-54
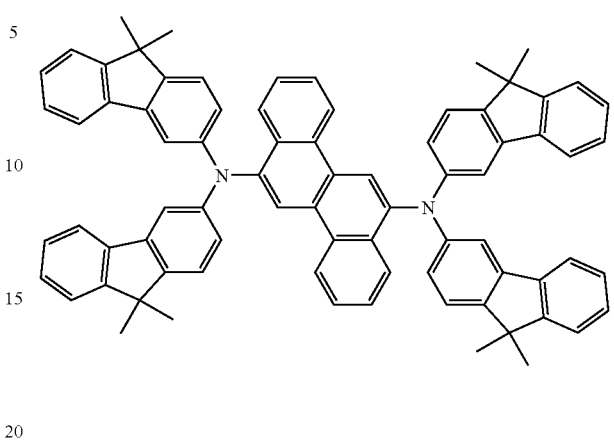
D-51
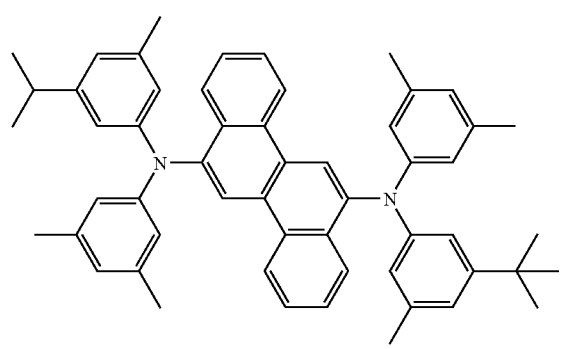
D-55
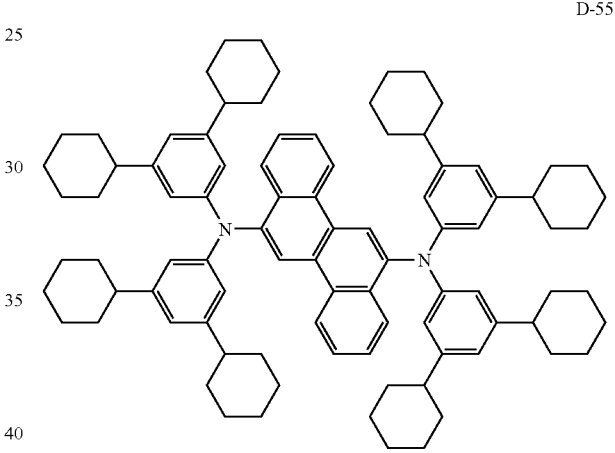
D-52
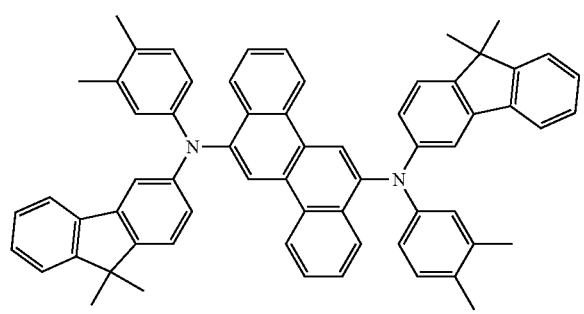
D-53
D-56
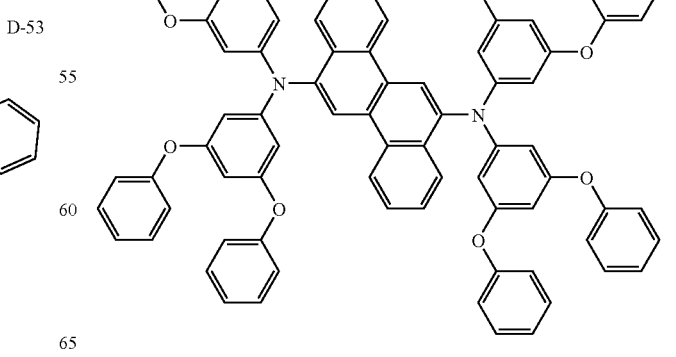

-continued

D-57

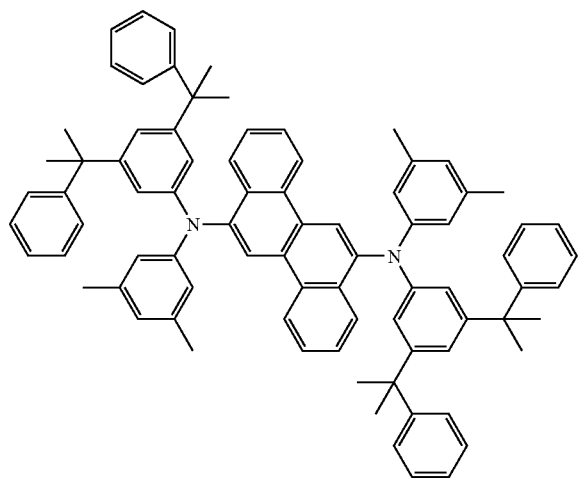

Among those, Compound (D-1), (D-2), (D-5), (D-6), (D-9), (D-17), (D-18), (D-20), (D-21), (D-22), (D-23), (D-25) and (D-26) are particularly preferable.

The following explains a process for manufacturing the aromatic amine derivatives of the present invention.

The process is not limited for producing the aromatic amine represented by the general formula (1), therefore, a well known process can be applied; for example, 6,12-dibromochrysene is aminated with diarylamine so as to produce the aromatic amine derivative by applying the process described in Rev. Roum. Chim., 341907 (1989), M. D. Bancia et al.

The aromatic amine derivative represented by the general formula (1) comprises a diaminochrysene structure which is a center for light emission and is bonded with a substituted benzene ring. Therefore, association between the derivatives is avoidable and a longer lifetime is exhibited. When the above substituent is two or more, association between the derivatives is more avoidable and a further longer lifetime is exhibited. In addition, the derivative exhibits strong fluorescence at a solid state, excellent light emission and fluorescence quantum efficiency of 0.3 or larger. Further, since it has a splendid hole injecting capability and a hole transportation capability from a metal electrode or an organic thin film layer, and also electron injecting capability and electron transportation capability from a metal electrode or an organic thin film layer, it can be used for a light emitting material of an organic EL device, particularly for a effective doping material. In addition, other hole transportation material, electron transportation material or doping material may be used.

The organic EL device of the present invention means a device comprising at least one organic thin film layer formed between an anode and a cathode. In the case based on a single layer, a light emitting layer is provided between an anode and a cathode. A light emitting layer contains a light emitting material and also may contain a hole injecting material or an electron injecting material so as to transport holes injected from the anode or electrons injected from the cathode.

Since the aromatic amine derivative exhibits high light emission capability and has splendid hole injecting capability/hole transportation capability and also electron injecting capability/electron transportation capability, it can be used for a light emitting layer as a light emitting material or a doping material. In the organic EL device of the present invention, it is preferable that a light emitting layer contains the organic amine derivative, and the content thereof is generally 0.1 to 20% by weight, more preferably 1 to 10% by weight.

Further, since the aromatic amine derivative exhibits high hole transportation capability and electron transportation capability as well as extremely high fluorescence quantum efficiency, and also can be formed into a uniform film, a light emitting layer may be formed by itself. In addition, in an organic EL device of the present invention comprising at least two of organic thin film layers including a light emitting layer sandwiched between a pair of electrode consisting of an anode and a cathode, it is preferable that an organic layer comprising the aromatic amine derivative as the main component thereof is placed between the anode and the cathode. The organic layer includes a hole injecting layer, a hole transporting layer and so forth.

More further, when the aromatic amine derivative is contained as a doping material, it is preferable that at least a derivative selected from anthracene derivatives represented by the general formulae (3) and (4), and a pyrene derivative represented by the general formula (5) is contained as a host material.

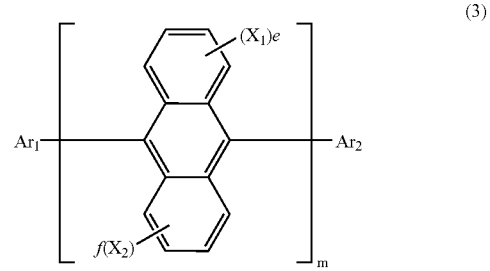

(3)

In the general formula (3), $X_1$ and $X_2$ each independently represents a hydrogen atom, a substituted or unsubstituted alkyl group having carbon atoms of 1 to 50, a substituted or unsubstituted aryl group having ring carbon atoms of 5 to 50, a substituted or unsubstituted aralkyl group having ring carbon atoms of 6 to 50, a substituted or unsubstituted cycloalkyl group having ring carbon atoms of 3 to 50, a substituted or unsubstituted alkoxyl group having ring carbon atoms of 1 to 50, a substituted or unsubstituted aryloxy group having ring carbon atoms of 5 to 50, a substituted or unsubstituted arylamino group having ring carbon atoms of 5 to 50, a substituted or unsubstituted alkylamino group having carbon atoms of 1 to 20, a substituted or unsubstituted hetero ring group having ring carbon atoms of 5 to 50 or a halogen atom. e and f each independently represents an integer of 0 to 4. When e and f are two or more, $X_1$ and $X_2$ may be the same with or different from each other.

$Ar_1$ and $Ar_2$ each independently represents a substituted or unsubstituted aryl group having ring carbon atoms of 5 to 50, a substituted or unsubstituted hetero ring group having ring carbon atoms of 5 to 50, and at least one of $Ar_1$ and $Ar_2$ represents a substituted or unsubstituted aryl group containing a hetero ring having ring carbon atoms of 10 to 50. m represents an integer of 1 to 3. When m is 2 or more, the groups in [ ] may be the same with or different from each other.

The specific examples of each group and substituent of $X_1$ and $X_2$, and, $Ar_1$ and $Ar_2$ are similar to the ones shown in the general formula (1).

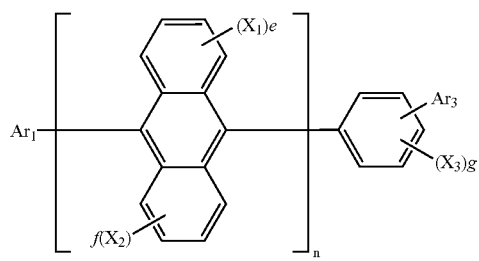

(4)

In the general formula (4), $X_1$ to $X_3$ each independently represents hydrogen atom, a substituted or unsubstituted alkyl group having carbon atoms of 1 to 50, a substituted or unsubstituted aryl group having ring carbon atoms of 5 to 50, a substituted or unsubstituted aralkyl group having ring carbon atoms of 6 to 50, a substituted or unsubstituted cycloalkyl group having ring carbon atoms of 3 to 50, a substituted or unsubstituted alkoxyl group having ring carbon atoms of 1 to 50, a substituted or unsubstituted aryloxy group having ring carbon atoms of 5 to 50, a substituted or unsubstituted arylamino group having ring carbon atoms of 5 to 50, a substituted or unsubstituted alkylamino group having carbon atoms of 1 to 20, a substituted or unsubstituted hetero ring group having ring carbon atoms of 5 to 50 or a halogen atom. e, f and g each independently represents an integer of 0 to 4. When e, f and g are two or more, $X_1$, $X_2$ and $X_3$ are the same with or different from each other. $Ar_1$ represents a substituted or unsubstituted aryl group containing a condensed ring having ring carbon atoms of 10 to 50, and $Ar_3$ represents a substituted or unsubstituted aryl group having ring carbon atoms of 5 to 50. n represents an integer of 1 to 3. When n is 2 or more, the groups in [ ] may be the same with or different from each other. The specific examples of each group and substituent of $X_1$, $X_2$, $X_3$, $Ar_1$ and $Ar_3$ are similar to the ones shown in the general formula (1).

The specific examples of anthracene derivatives represented by the general formulae (3) and (4) include the following, but not limited thereto;

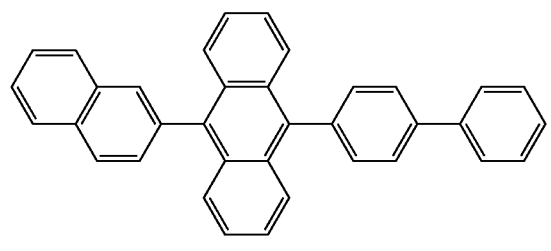

AN1

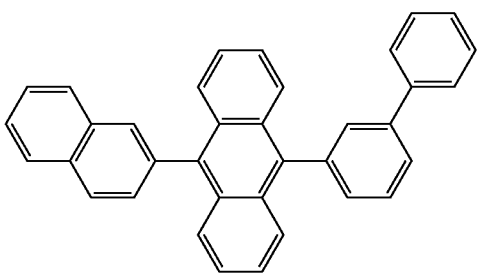

AN2

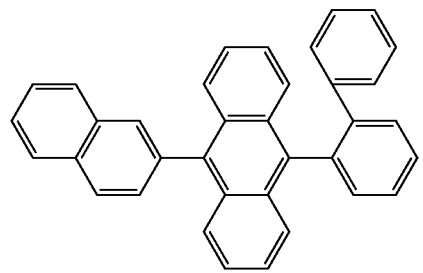

AN3

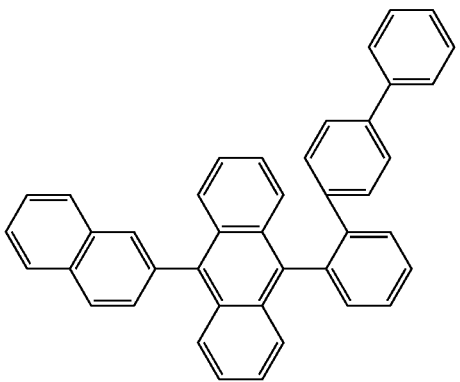

AN4

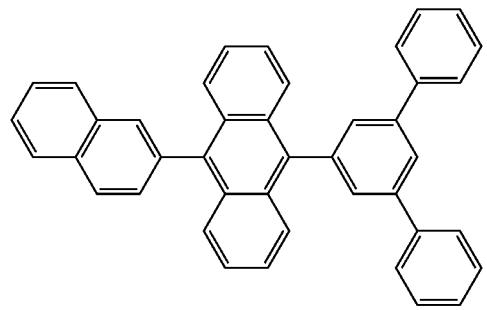

AN5

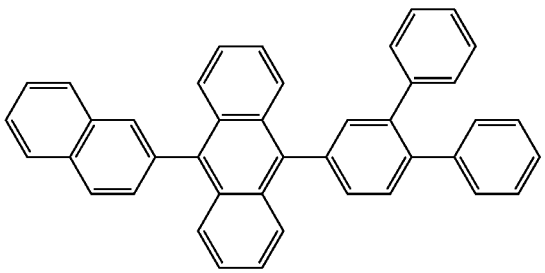

AN6

-continued
AN7
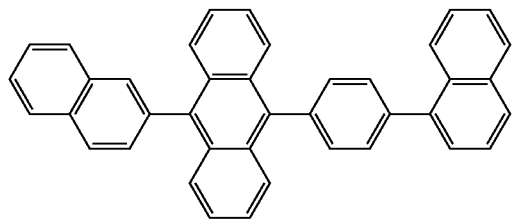
AN8
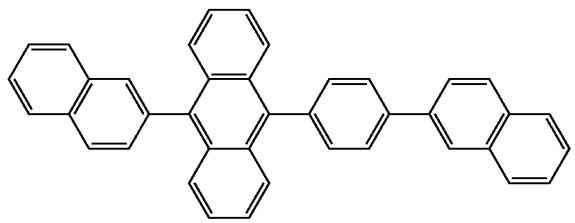
AN9
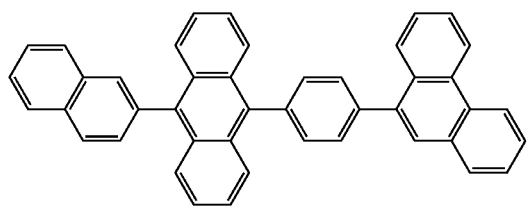
AN10
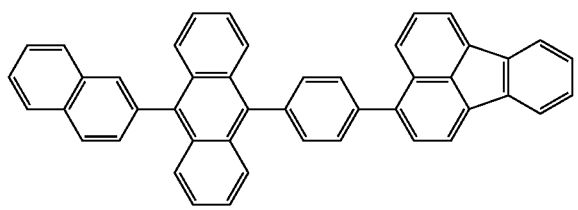
AN11
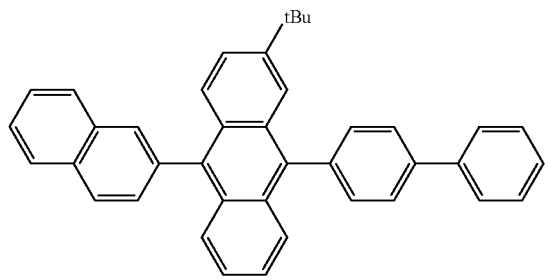
AN12
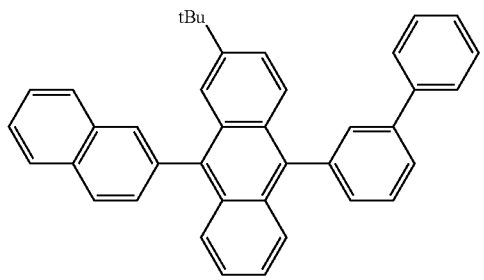
AN13
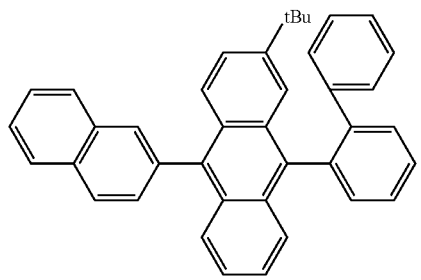
AN14
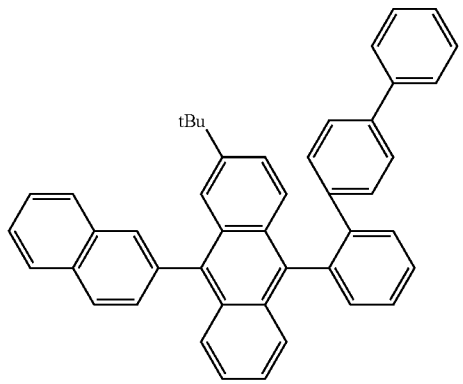
AN15
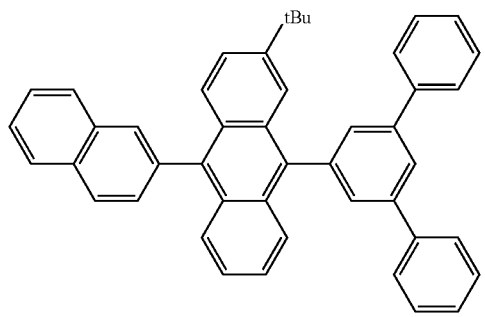
AN16
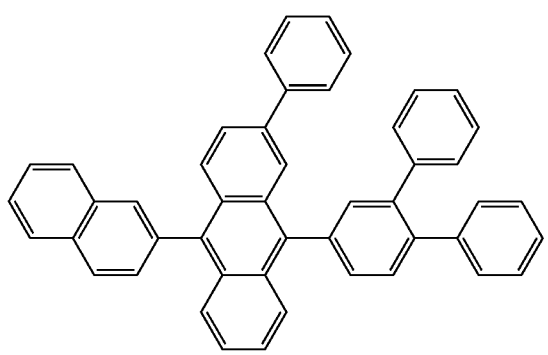

-continued
AN17
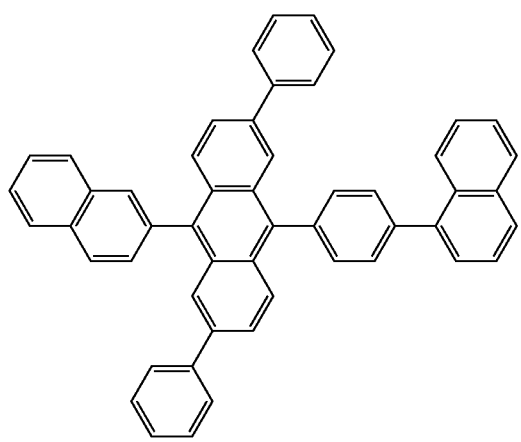
AN18
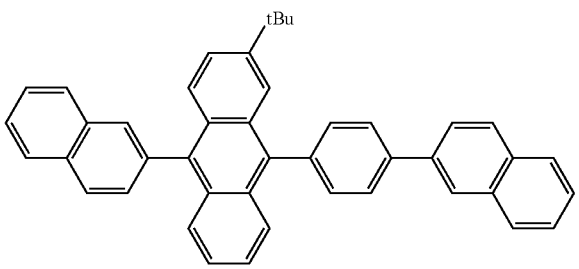
AN19
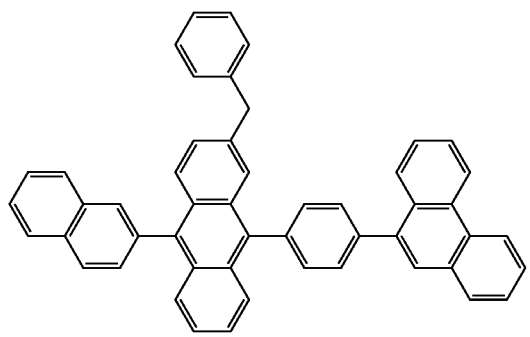
AN20
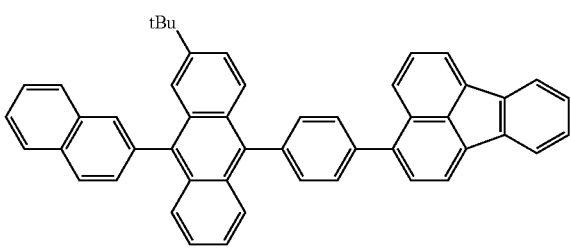
AN21
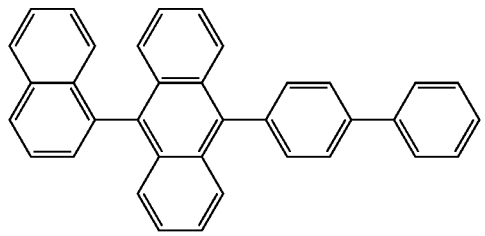
AN22
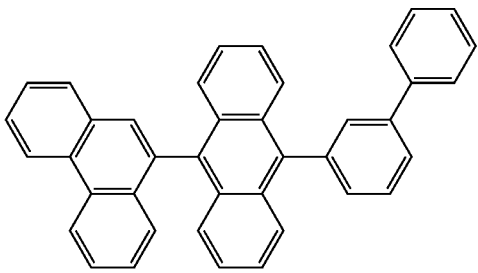
AN23
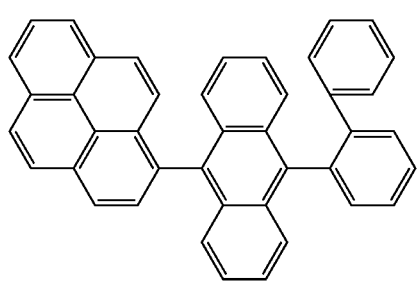
AN24
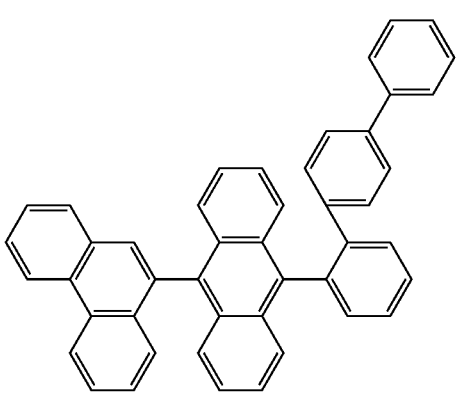

-continued
AN25
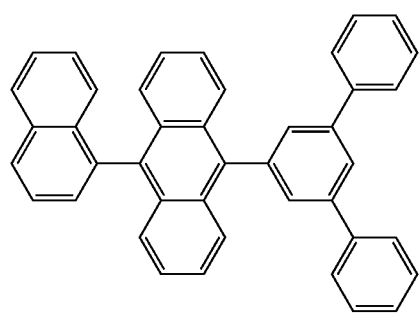
AN26
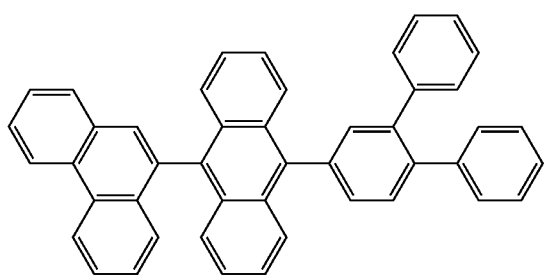
AN27
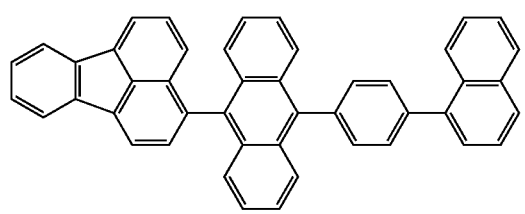
AN28
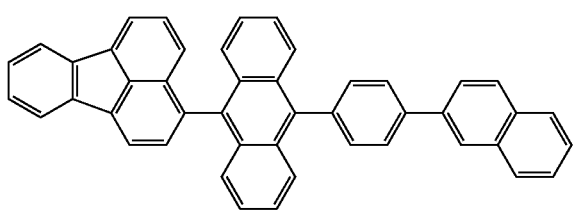
AN29
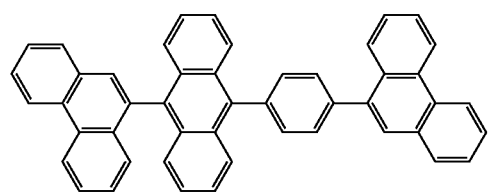
AN30
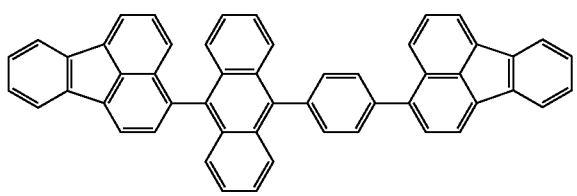
AN31
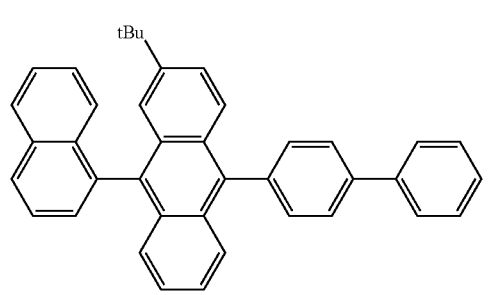
AN32
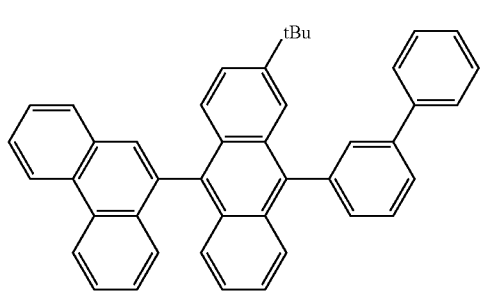
AN33
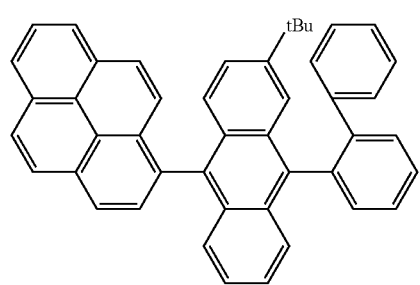
AN34
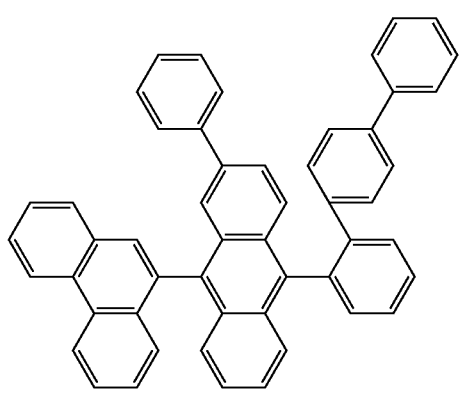

-continued
AN35
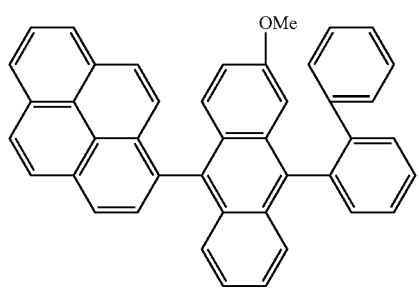
AN36
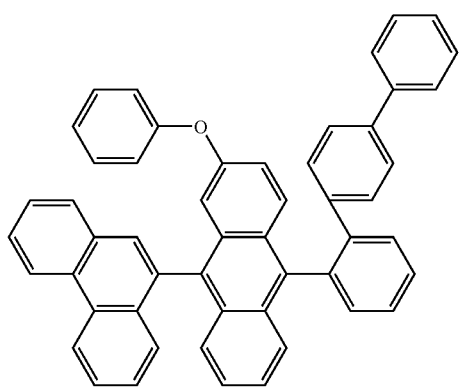
AN37
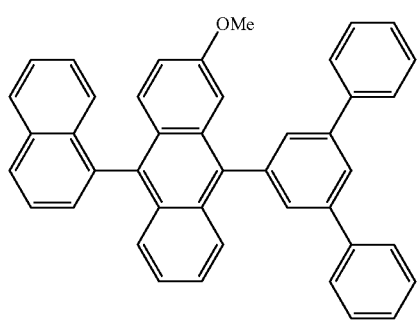
AN38
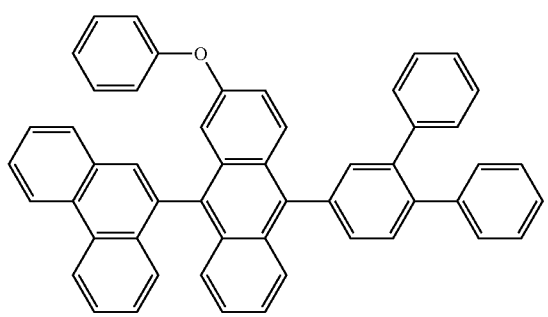
AN39
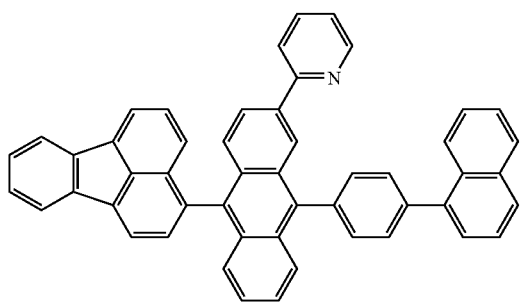
AN40
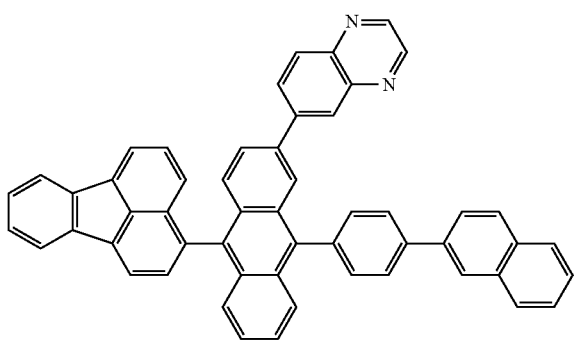
AN41
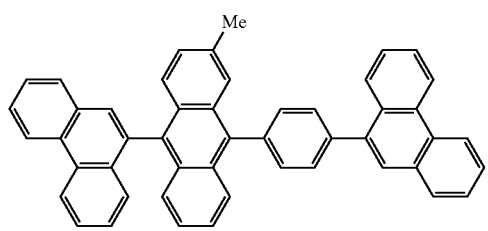
AN42
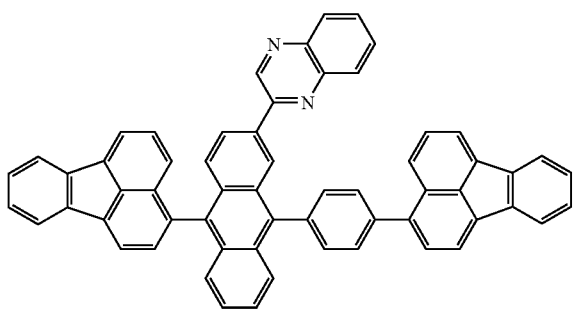

-continued
AN43
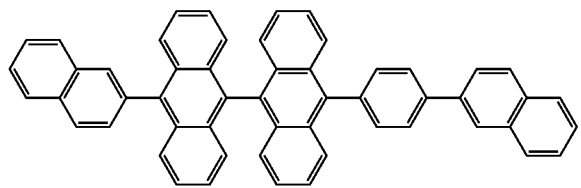
AN44
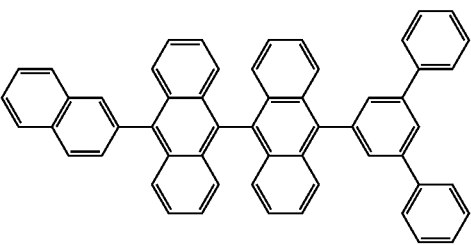
AN45
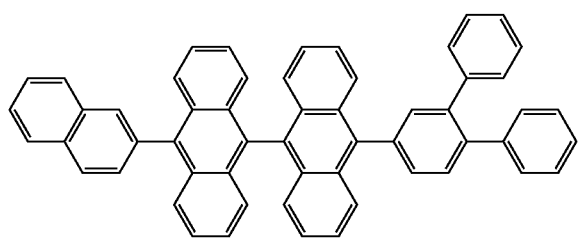
AN46
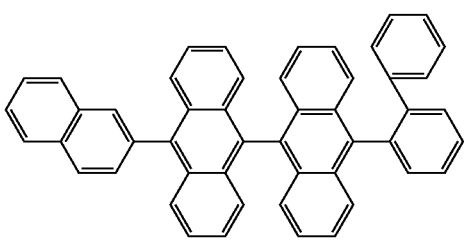
AN47
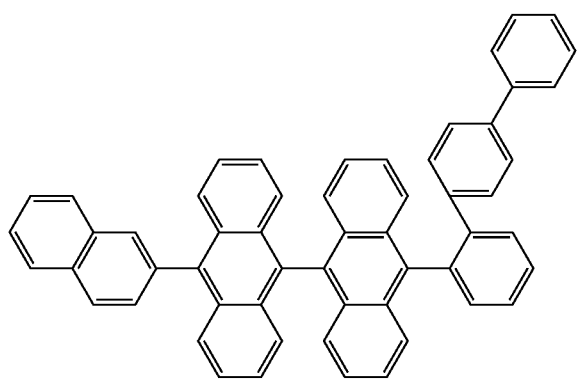
AN48
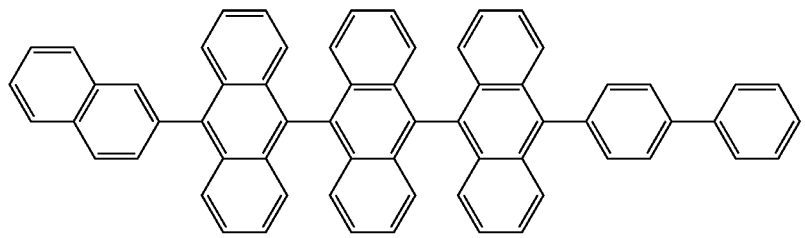
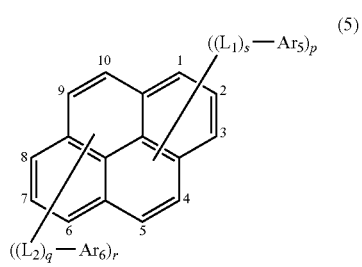
(5)

Ar$_5$ and Ar$_6$ in the general formula (5) each independently represents a substituted or unsubstituted aryl group having ring carbon atoms of 6 to 50.

L$_1$ and L$_2$ each independently represents a substituted or unsubstituted phenylene group, a substituted or unsubstituted naphthalene group, a substituted or unsubstituted fluorenylene group or a substituted or unsubstituted dibenzosilolylene group, s represents an integer of 0 to 2, p represents of an integer of 1 to 4, q represents an integer of 0 to 2 and r represents an integer of 0 to 4, further, L$_1$ or Ar$_5$ bonds to any one of 1 to 5 position of pyrene, and L$_2$ or Ar$_6$ bonds to any one of 6 to 10 position thereof, however, when p+r is an even number, Ar$_5$, Ar$_6$, L$_1$ and L$_2$ satisfy a following requirement (1) or a requirement (2):

(1) Ar$_5$≠Ar'$_6$ and/or L$_1$≠L$_2$, wherein ≠ means that each group has a different structure,
(2) when Ar$_5$=Ar$_6$ and L$_1$=L$_2$, (2-1) s≠q and/or p≠r, or (2-2) when s=q and p=r,
(2-2-1) both L$_1$ and L$_2$ or pyrene bond respectively to a different position of Ar$_5$ and Ar$_6$, or
(2-2-2) both L$_1$ and L$_2$ or pyrene bond respectively to the same position of Ar$_5$ and Ar$_6$ excluding a case where both L$_1$ and L$_2$ or both Ar$_5$ and Ar$_6$ bond respectively to 1 and 6, or 2 and 7 positions thereof.

The specific examples of each group and substituent of Ar$_5$, Ar$_6$, L$_1$, and L$_2$ are similar to the ones shown in the general formula (1).

The specific examples of the pyrene derivatives represented by the general formula (5) include the following, but not limited thereto;

P1

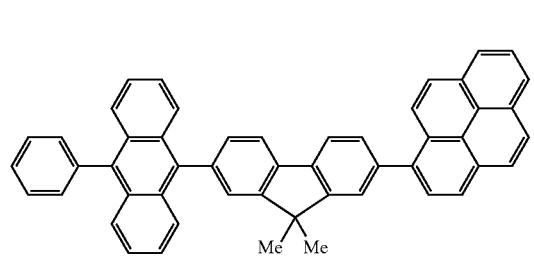

P2

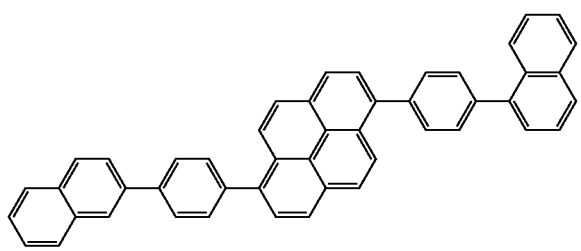

P3

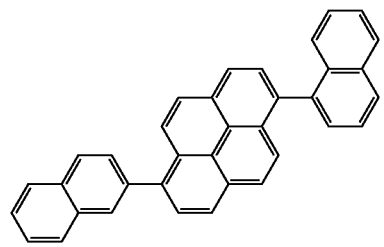

P4

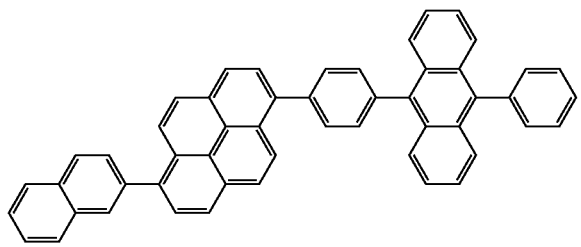

P5

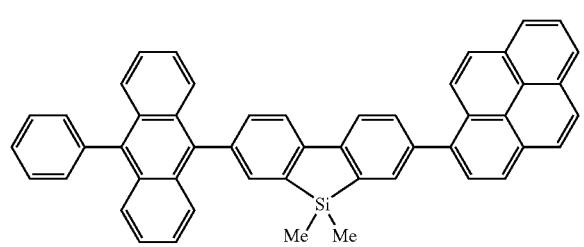

P6

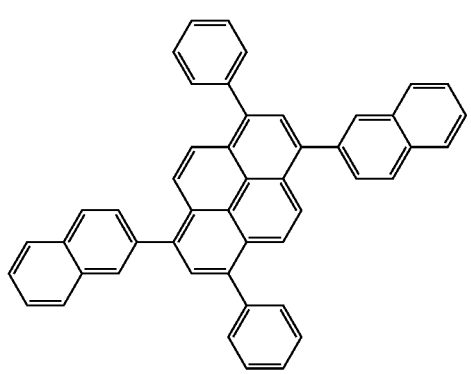

-continued
P7
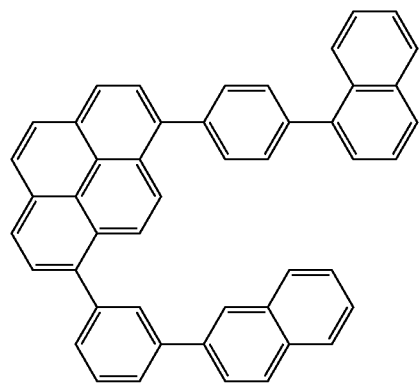
P8
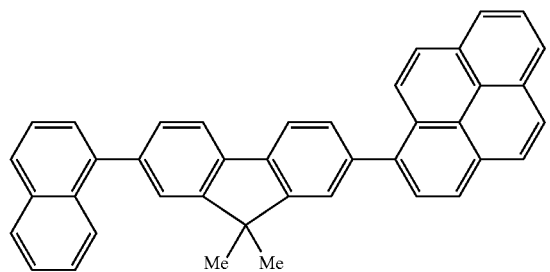
P9
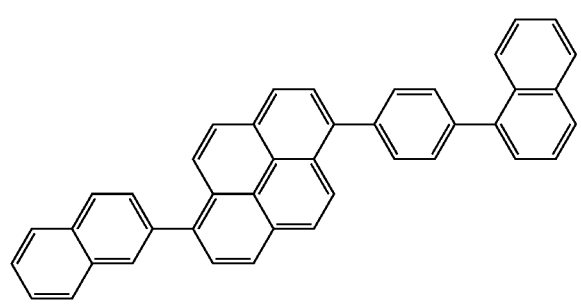
P10
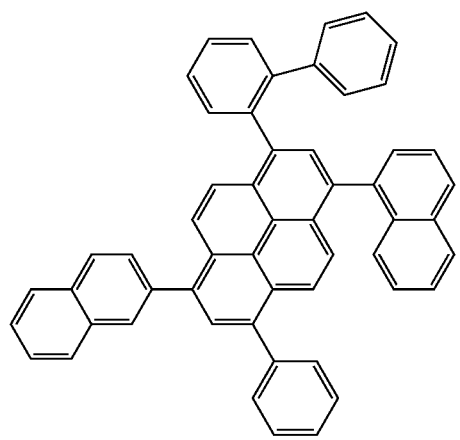
P11
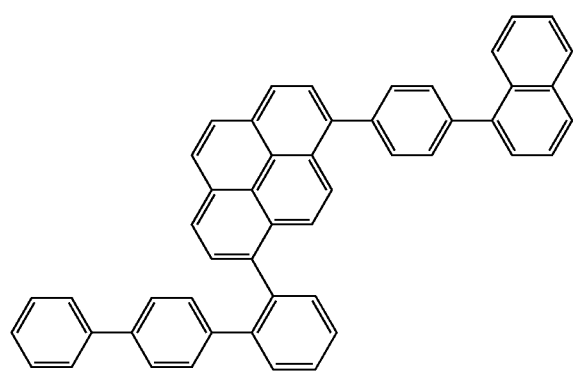
P12
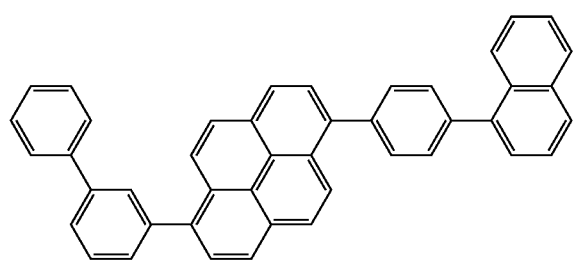
P13
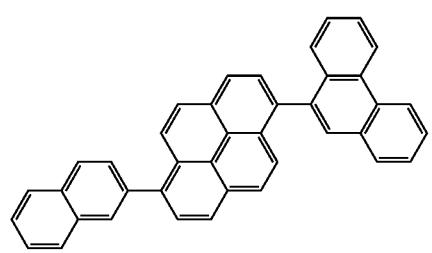
P14
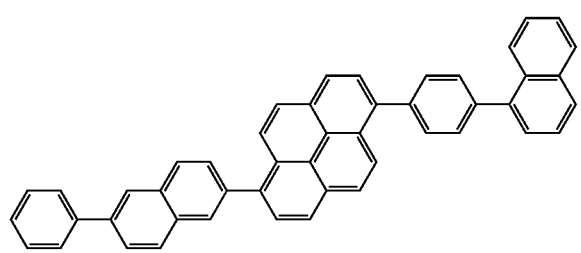

-continued
P15
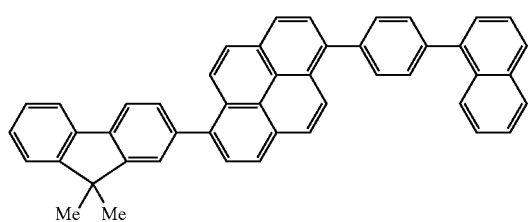
P16
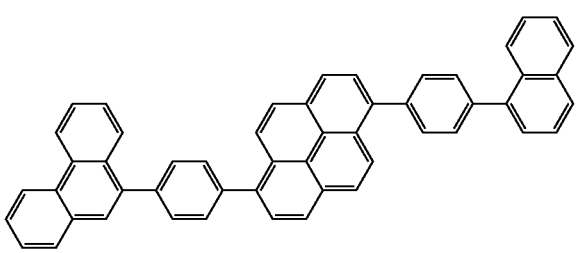
P17
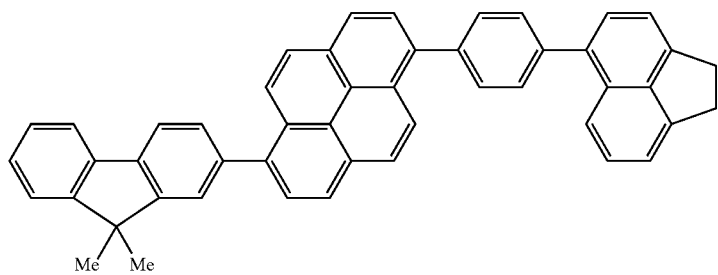
P18
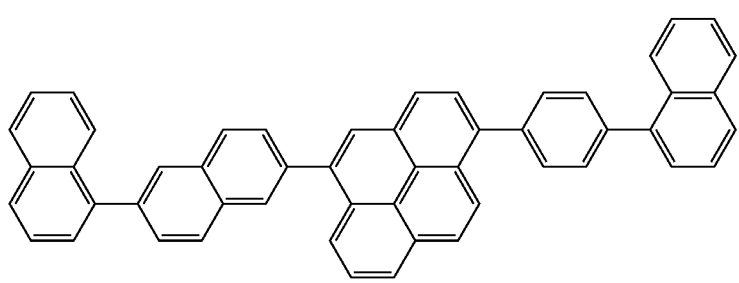
P19
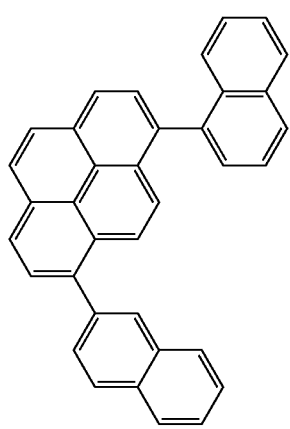
P20
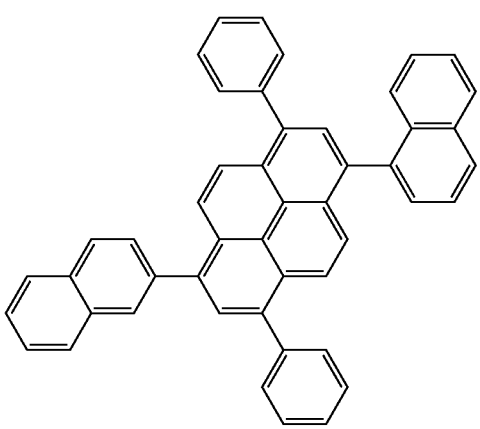

-continued
P21

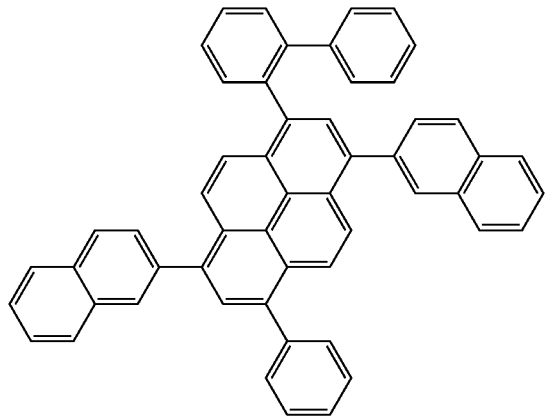

The organic EL device comprising the plural organic thin film layers of the present invention includes a laminated structure such as an anode/a hole injecting layer/a light emitting layer/a cathode, an anode/a light emitting layer/an electron injecting layer/a cathode, and an anode/a hole injecting layer/a light emitting layer/an electron injecting layer/a cathode. In addition to the aromatic amine derivatives, if required, well known light emitting materials, doping materials, hole injecting materials and electron injecting materials may be added into the plural layers. By making the organic thin film layer into a plural layer structure, it is possible to prevent luminance or lifetime of an organic EL device from decreasing due to quenching. If required, a light emitting material, a doping material, a hole injecting material or an electron injecting material may be used as a combination thereof. In addition, it is also possible to improve emission luminance or current efficiency, and obtain red light emission or blue light emission. Further, a hole injecting layer, a light emitting layer and an electron injecting layer each may be formed into a layer structure having two or more layers. In the case of a hole injecting layer, a layer, into which holes are injected from an electrode, is called as a hole injection layer, and a layer, which receives holes for a hole injecting layer and transports them to a light emitting layer, is called as a hole transporting layer.

Correspondingly, in the case of an electron injecting layer, a layer, into which electrons are injected from an electrode, is called as an electron injection layer, and a layer, which receives electrons from an electron injecting layer and transports them to a light emitting layer, is called as an electron transporting layer. Above each layer is selected and applied based on a factor such as energy level and heat resistance of materials, and degree of adhesion to an organic layer or an metal electrode.

A host material or a dopant other than the aforementioned general formulae (3) to (5) being able to be used together with the aromatic amine derivatives includes, condensed multiaromatic compounds and derivatives thereof such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethinyl)anthracene and 1,4-bis(9'-ethinylanthracene)benzene, an organic metal complexes such as tris(8-quinolinnolate)aluminium, bis-(2-methyl-8-quinolinolate)-4-(phenylphenolinate)aluminum, a triarylamine derivative, a styryl amine derivative, a stilbene derivative, a coumarin derivative, a pyran derivative, an oxazone derivative, a benzothiazole derivative, a benzoxazole derivative, a benzoimidazole derivative, a pyrazine derivative, a cinnamic acid ester derivative, a diketonepyrrolopyrrole derivative, an acridone derivative and a quinacridone derivative, but not limited thereto.

It is preferable for a hole injecting material that a compound exhibits hole transportation capability, a hole injection effect from an anode, a splendid hole injection effect to a light emitting layer or a light emitting material, prevents exciton generated in a light emitting layer from transporting to an electron injecting layer or an electron injecting layer, and has excellent capability of forming a thin film. Specific examples thereof include a phthalocyanine derivative, a naphthalocyanine derivative, a porphyrin derivative, oxazole, oxadiazole, triazole, imidazole, imidazolone, imidazolethion, pyrazoline, pyrazolone, tetrahydroimidazole, oxazole, oxadiazole, hydrazone, acylhydrazone, polyarylalkane, stilbene, butadiene, benzidine based triphenyl amine, styrylamine based triphenyl amine, diamine based triphenylamine and the like, and their derivatives, and also polymer materials such as polyvinylcarbazole, polysilane and electroconductive polymer, but not limited thereto.

More effective hole injecting material includes a aromatic tertiary amine derivative and a phthalocyanine derivative among hole injecting materials usable for the organic EL device.

The tertiary amine derivative includes, for example, triphenylamine, tritolylamine, tridiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1, 1'-biphenyl-4,4'-diamine, N,N'-diphenyl-N,N'-dinaphthyl-1,1'-biphenyl-4,4'-diamine, N,N'-dinaphenyl-N,N'-dinaphthyl-1,1'-biphenyl-4,4'-diamine, N,N'-(methylphenyl)-N,N-(4-n-butylphenyl)-phenanthrene-9,10-diamine, N,N-bis(4-di-4-tolylaminephenyl)-4-phenylcyclohexane, or oligomer or polymer having a backbone of these aromatic tertiary-amines, but not limited thereto.

Phthalocyanine (Pc) derivatives include, for example, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O-GaPc and naphthalocyanine derivatives, but not limited thereto. Further, it is preferable that the organic EL device of the present invention contains a layer such as the hole transportation layer or the hole injecting layer, which comprises the aromatic tertiary amine derivatives and/or the phthalocyanine derivatives, for example. The layer is formed between the light emitting layer and the anode.

It is preferable for an electron injecting material that a compound exhibits electron transportation capability, an electron injection effect from a cathode, a splendid electron injection effect to a light emitting layer or a light emitting material, prevents exciton generated in a light emitting layer from transporting to a hole injecting layer, and has a excellent capability of forming a thin film. Specific examples thereof include fluorene, anthraquinodimethane, diphenoquinone, thiopyrandioxide, oxazole, oxadiazole, triazole, imidazole, perylenetetracarboxylic acid, fluorenylidenmethane, anthraquinodimethane, anthrone and derivetives thereof, but not limited thereto.

In addition, it is possible to increase desensitization by adding an electron receptible substance into a hole injecting material and by adding an electron donating substance into an electron injecting material.

An effective electron injecting material for the organic EL device includes a metal complex compound and a 5 member ring derivative having a nitrogen atom. The metal complex compound includes, for example, 8-hydroxyquinolinate lithium, bis(8-hydroxyquinolinate)zinc, bis(8-hydroxyquinolinate)copper, bis(8-hydroxyquinolinate)manganese, tris(8-hydroxyquinolinate)aluminum, tris(2-methyl-8-hydroxyquinolinate)aluminum, tris(8-hydroxyquinolinate)gallium, bis(10-hydroxybenzo[h]quinolinate)beryllium, bis(10-hydroxybenzo[h]quinolinate)zinc, bis(2-methyl-8-hydroxyquinolinate)chlorogallium, bis(2-methyl-8-quinolinate)(o-cresolate)gallium, bis(2-methyl-8-quinolinate)(1-naphthola)aluminum, bis(2-methyl-8-quinolinate)(2-naphtholate)gallium and the like, but not limited thereto.

The 5 member ring derivative having a nitrogen atom includes, for example, derivatives of oxazole, thiazole, oxadiazole, thiadiazole and triazole. Specific examples thereof include 2,5-bis(1-phenyl)-1,3,4-oxazole, dimethylPOPOP, 2,5-bis(1-phenyl)-1,3,4-thaizole, 2,5-bis(1-phenyl)-1,3,4-oxadiazole, 2-(4'-ter-butylphenyl)-5-bis(4"-biphenyl)-1,3,4-oxadiazole, 2,5-bis(1-naphthyl)-1,3,4-oxadiazole, 1,4-bis[2-(5-phenyloxadiazolyl)]benzen, 1,4-bis[2-(5-phenyloxadiazolyl-4-tert-butylbenzen], 2-(4'-tert-butylphenyl)-5-(4"-biphenyl)-1,3,4-thiadiazole, 2,5-bis(1-naphthyl)-1,3,4-thiaziazole, 1,4-bis[2-(5-phenylthiadiazolyl)]benzen, 2-(4'-tert-butylphenyl)-5-(4"-biphenyl)-1,3,4-triazole, 2,5-bis(1-naphtyl)-1,3,4-triazole, 1,4-bis[2-(5-phenyltriazolyl)]benzene, but not limited thereto.

A light emitting layer of the organic EL device of the present invention may contain at least one selected from a light emission material, a doping material, a hole injecting material and an electron injection material in the same layer in addition to at least an aromatic amine derivative selected from the general formula (1). In addition, an organic EL device obtained by the present invention may be provided with a protective layer on the surface thereof, or covered entirely by silicon oil, resin and the like so as to improve the stability to temperature, moisture, atmosphere and so forth.

A preferable electroconductive material employed for an anode of the organic EL device comprises a material having a work function larger than 4 eV. Examples thereof include carbon, aluminum, vanadium, iron, cobalt, nickel, tungsten, silver, gold, platinum, vanadium and alloy thereof, and also a metaloxide such as tin oxide to be used for an ITO substrate and indium oxide to be used for a NESA substrate, and further organic conductive resin such as polythiophene and polythiol.

A preferable electroconductive material employed for a cathode of the organic EL device comprises a material having a work function smaller than 4 eV. Examples thereof include magnesium, calcium, tin, zinc, titanium, yttrium, lithium, ruthenium, manganese, aluminum, lithium fluoride and alloy thereof, but not limited thereto.

Typical examples of the alloy include magnesium-silver alloy, magnesium-indium alloy and lithium-aluminum alloy, but not limited thereto. The ratio of the alloy components may selected properly by controlling the temperature of deposition source, atmosphere, vacuum level and the like on deposition.

An anode and a cathode each may be formed by two or more layers if required.

The organic EL device on the present invention can be preferably provided with at least a substantial transparent side; the transparent means transparent in wavelength zone of light emission. Further, a substrate can be preferably transparent. A transparent electrode having designated translucency is provided with a method such as vapor deposition, sputtering and the like by using the aforementioned conductive materials. An electrode of a light emitting surface has preferably a light transmittance of 10% or greater. As a substrate having mechanical and thermal strength, and transparency, glass sheet and transparent resin film are advantageously employed, but it should not be construed as limiting it. Specific examples of the transparent resin film include resin film made of polyethylene ethylene-vinyl acetate copolymer, ethylene-vinylalcohol copolymer, polypropyrene, polystyrene, polymethylmethacrylate, poluvinylchloride, polyvinylalcohol, polyvinylbutyral, nylon, polyether ether ketone, polysulfone, polyether sulfone, tetrafluoroethylene-perfluoroalkylvinylether copolymer, polyvinylfluoride, tetrafluoroethylene-ethylene copolymer, tetrafluoropropyrene-hexfluoropropyrene copolymer, polychlorotrifluoroethylene, polyvinylidenefluoride, polyesters, polycarbonate, polyurethene, polyimide, polyetherimide and the like.

The layers in the organic EL device of the present invention can be formed by any one of the dry film forming processes such as the vacuum vapor deposition process, the sputtering process, the plasma process, the ion plating process, or the wet film forming process such as the spin coating process, the dipping process and the flow coating process. The thickness of each layer of the organic thin film layers can be provide with a reasonable thickness, but not particularly limited. An excessively thick layer requires a high applied voltage results in decreasing the current efficiency, and an excessively thin layer tends to have defects such as pin holes. In general, the range from 5 nm to 10 µm in thickness thereof is preferable, and the range from 10 nm to 0.2 µm in thickness thereof is more preferable.

In the case of the wet film forming process, a film for each layer is made of a material dissolved or dispersed in a appropriate solvent such as ethanol, chloroform, tetrahydrofuran and dioxane, but not limited thereto. In addition, in any one of the organic thin film layers, a appropriate resin or an additive may be used so as to improve film forming capability, prevent from forming pin hole in the thin film and so forth. Examples of the employable resins include an insulating resin such as polystyrene, polycarbonate, polyarylate, polyester, polyamide, polyurethane, polysulfone, polymethylmethacrylate, polymethylacrylate, cellulose and copolymer thereof, a photoconductive resin such as poly-N-vinylcarbazole and polysilane, and an electroconductive resin such as polythiophene and polypyrrole. Further, the additives include an antioxidant, ultraviolet absorbent, plasticizer and the like.

The organic EL device of the present invention can be used for a flat light emitter of a flat panel display for a television hanging on walls, a backlight for a copying machine, a liquid crystal display, a light source for instruments, an indicator, a marker lamp and the like. In addition, the materials of the present invention may be used in the fields of a photo conductor of electrophotography, photoelectric transfer devices, solar cells, image sensors and the like.

EXAMPLE

This invention will be described in further detail with reference to the examples.

Synthesis Example 1

Synthesis of Compound (D-1)

Figure 2:
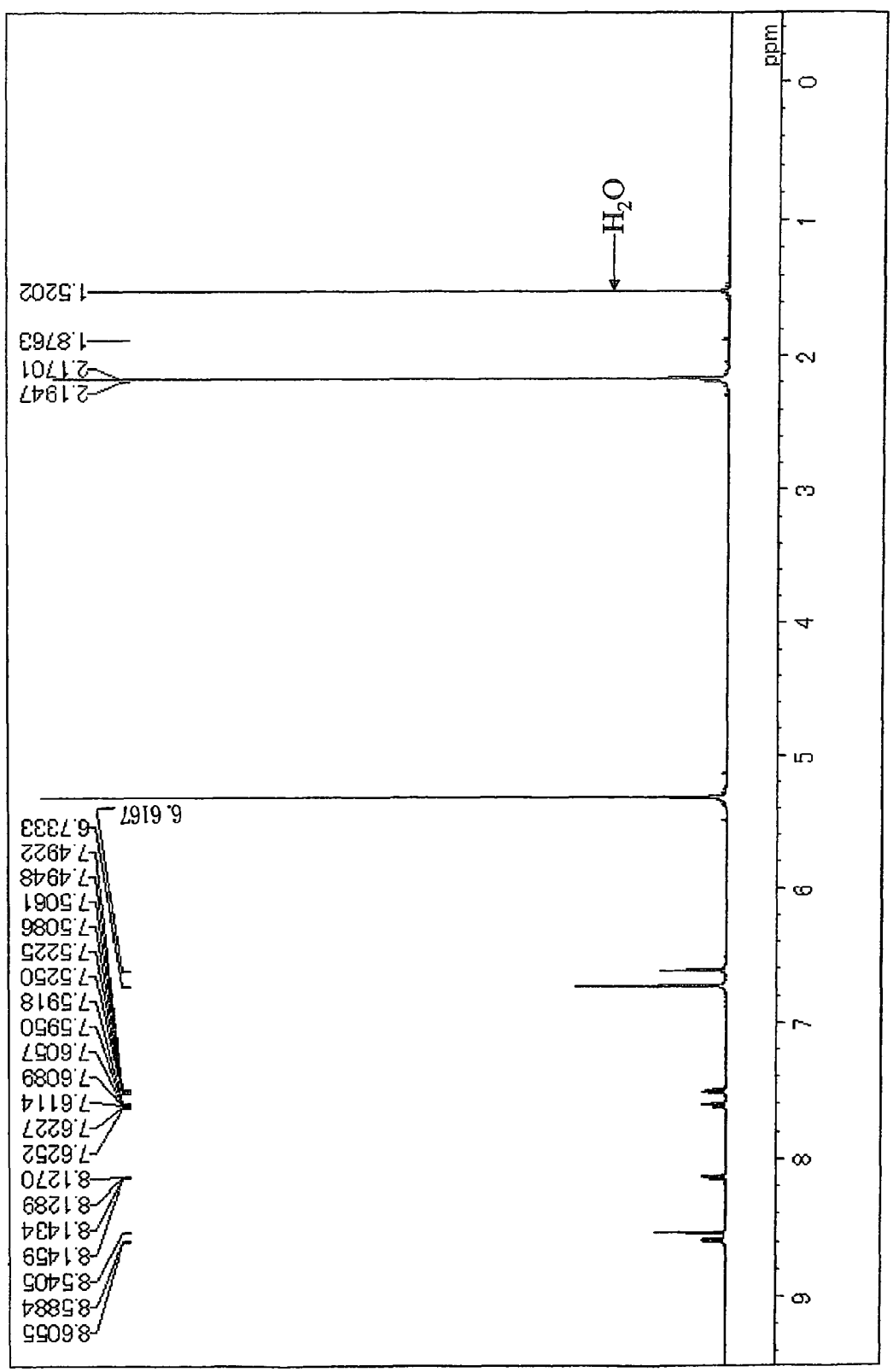
FIG. 2

Under the atmosphere of argon gas, into a three neck flask of 300 ml equipped with a condenser, 3.8 g (10 mmol) of 6, 12-dibromochrysene, 5.6 g (25 mmol) of bis(3,5-dimethylphenyl)amine, 0.03 g (1.5 mol%) of palladium acetate, 0.06 g (3 mol%) of tri-t-butylphosphine, 2.4 g (25 mmol) of t-sodiumbutoxide and 100 ml of dried toluene were placed, and then stirred over night at 100 deg C. After completion of the reaction, the crystal precipitated was separated by filtration, followed by washing it with 50 ml of toluene and 100 ml of methanol, and then 6.6 g of pale yellow powder was obtained. It was confirmed that the product was Compound (D-2) by the measurements of 1H-NMR spectrum (FIG. 2) and FD-MS. Yield: 98%. In addition, the maximum absorption wave length was 405 nm and the maximum fluorescent wavelength was 450 nm when Compound obtained was measured in toluene solution.

Synthesis Example 2

Synthesis of Compound (D-2)

Under the atmosphere of argon gas, into a three neck flask of 300 ml equipped with a condenser, 3.8 g (10 mmol) of 6,12-dibromochrysene, 5.6 g (25 mmol) of bis(3,4-dimethylphenyl)amine, 0.03 g (1.5 mol %) of palladium acetate, 0.06 g (3 mol %) of tri-t-butylphosphine, 2.4 g (25 mmol) of t-sodiumbutoxide and 100 ml of dried toluene were placed, and then stirred over night at 100 deg C. After completion of the reaction, the crystal precipitated was separated by filtration, followed by washing it with 50 ml of toluene and 100 ml of methanol, and then 6.6 g of pale yellow powder was obtained. It was confirmed that the product was Compound (D-2) by the measurements of $^1$H-NMR spectrum (FIG. 2) and FD-MS. Yield: 98%. In addition, the maximum absorption wave length was 405 nm and the maximum fluorescent wavelength was 450 nm when Compound obtained was measured in toluene solution.

Synthesis Example 3

Synthesis of Compound (D-9)

Figure 3:
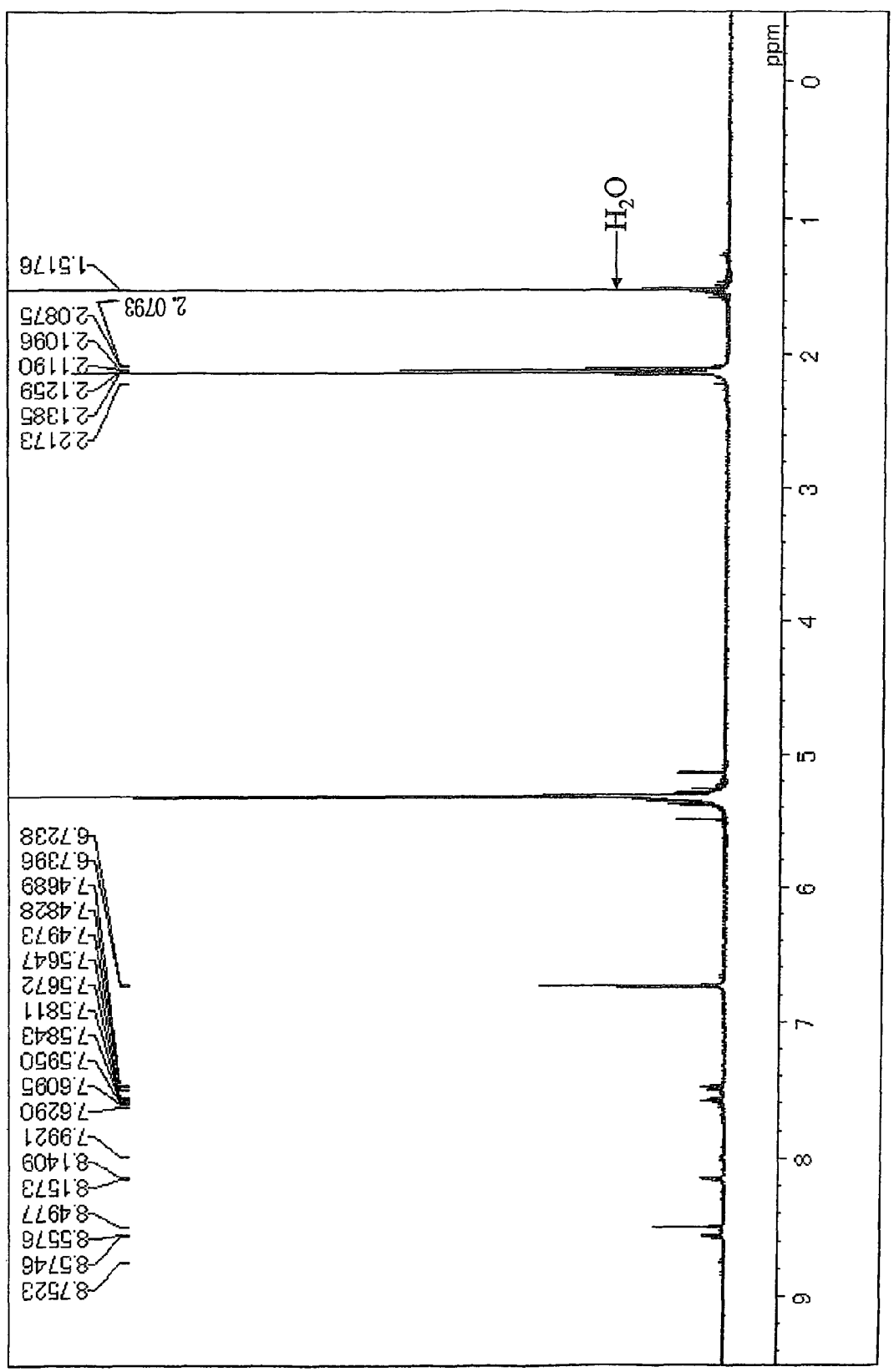
FIG. 3

Under the atmosphere of argon gas, into a three neck flask of 300 ml equipped with a condenser, 3.8 g (10 mmol) of 6,12-dibromochrysene, 6.3 g (25 mmol) of bis(3,4,5-trimethylphenyl)amine, 0.03 g (1.5 mol %) of palladium acetate, 0.06 g (3 mol %) of tri-t-butylphosphine, 2.4 g (25 mmol) of t-sodiumbutoxide and 100 ml of dried toluene were placed, and then stirred over night at 100 deg C. After completion of the reaction, the crystal precipitated was separated by filtration, followed by washing it with 50 ml of toluene and 100 ml of methanol, and then 7.6 g of pale yellow powder was obtained. It was confirmed that the product was Compound (D-9) by the measurements of $^1$H-NMR spectrum (FIG. 3) and FD-MS. Yield: 98%. In addition, the maximum absorption wave length was 416 nm and the maximum fluorescent wavelength was 463 nm when Compound obtained was measured in toluene solution.

Synthesis Example 4

Synthesis of Compound (D-23)

Figure 4:
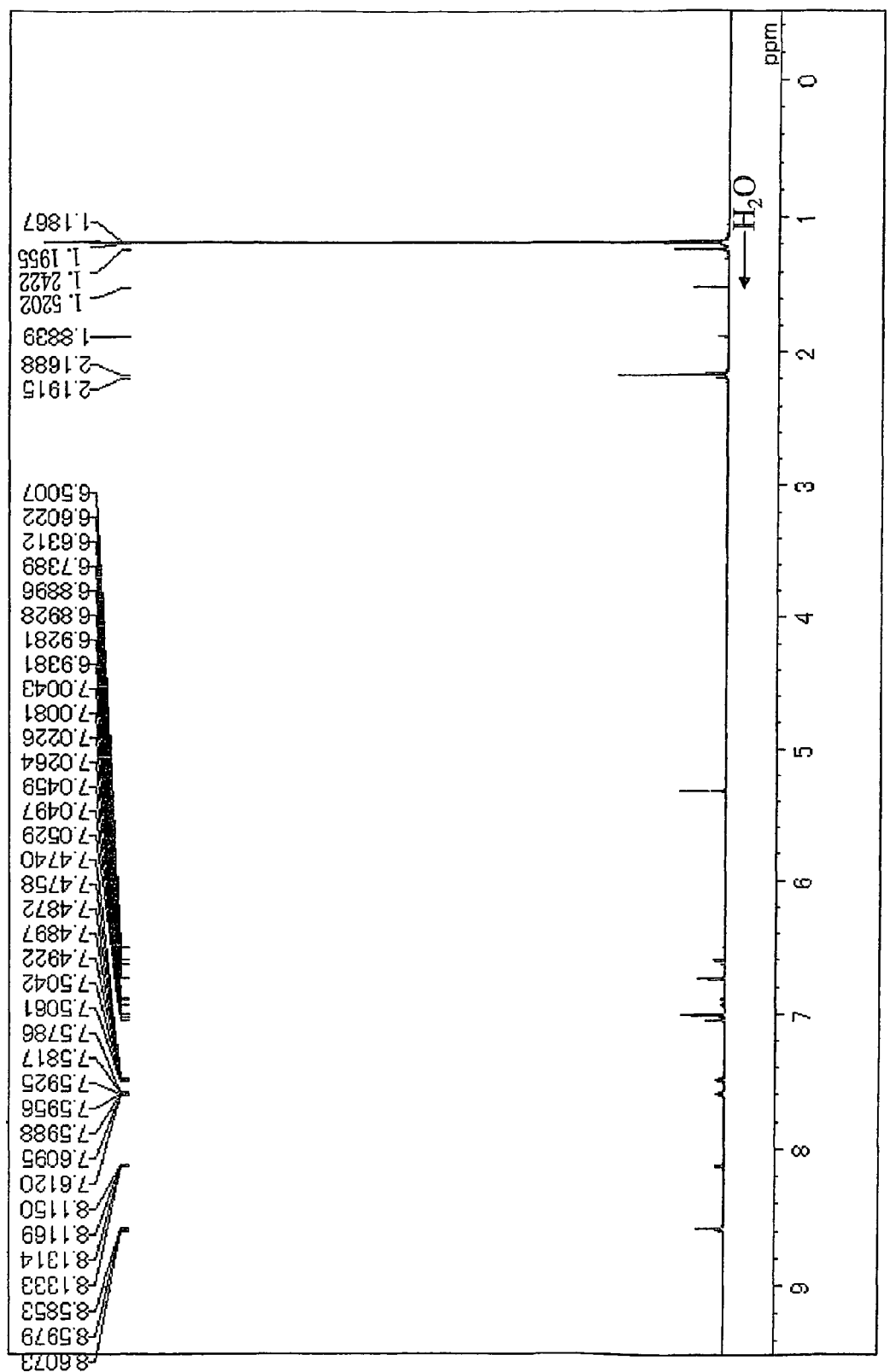
FIG. 4

Under the atmosphere of argon gas, into a three neck flask of 300 ml equipped with a condenser, 3.8 g (10 mmol) of 6,12-dibromochrysene, 7.7 g (25 mmol) of 3,5-dimethylphenyl-3',5'-di-t-butylphenylamine, 0.03 g (1.5 mol %) of palladium acetate, 0.06 g (3 mol %) of tri-t-butylphosphine, 2.4 g (25 mmol) of t-sodiumbutoxide and 100 ml of dried toluene were placed, and then stirred over night at 100 deg C. After completion of the reaction, the crystal precipitated was separated by filtration, followed by washing it with 50 ml of toluene and 100 ml of methanol, and then 7.6 g of pale yellow powder was obtained. It was confirmed that the product was Compound (D-23) by the measurements of $^1$H-NMR spectrum (FIG. 4) and FD-MS. Yield: 90%. In addition, the maximum absorption wave length was 408 nm and the maximum fluorescent wavelength was 454 nm when Compound obtained was measured in toluene solution.

Example 1

A transparent electrode comprising indium-tin oxide having 120 nm of film thickness was formed on a glass substrate of a 25 mm×75 mm×1.1 mm size. The glass substrate was cleaned by application ultraviolet light and ozone, and was place in a vacuum vapor deposition apparatus.

Firstly, N',N''-bis [4-(diphenylamino)phenyl]-N',N''-diphenylbiphenyl-,4'-diamine was deposited to be 60 nm thickness as the hole injecting layer, and then N,N,N'N'-tetrakis(4-biphenyl)-4,4'-benzidine was deposited thereon to be 20 nm as the hole transporting layer. Subsequently, 10,10'-bis[1,1',4',1'']terphenyl-2-yl-9,9'-bianthracenyl (BTBAN) and Compound (D-1) as a doping material at a weight ratio of BTBAN:D1=40:2 were deposited at once on the hole transporting layer to form the light emitting layer having 40 nm thickness. Then tris(8-hydroxyquinolinate)aluminum was deposited to be 20 nm thicknesses. Further, lithium fluoride was deposited to be 1 nm thickness and then aluminum was deposited to be 150 nm thicknesses. The aluminum/lithium fluoride performs as the cathode. The organic EL device was prepared as stated above.

The device was tested by passing electric current, a blue light emission with a current efficiency of 7.1 cd/A and an emission luminance of 710 cd/m$^2$ (maximum light emission wavelength: 466 nm) was observed at a voltage of 6.5 V and a current density of 10 mA/cm2. It was continuously tested by passing electric current at an initial luminance of 500 cd/m$^2$, the half lifetime was founded to be 16,000 hours.

Example 2

The organic EL device was fabricated similarly as Example 1 except that Compound (D-5) was used in place of Compound (D-1). The device was tested by passing electric current, a blue light emission with a current efficiency of 7.8 cd/A and an emission luminance of 780 cd/m$^2$ (maximum light emission wavelength: 468 nm) was observed at a voltage of 6.5 V and a current density of 10 mA/cm2. It was continuously tested by passing electric current at an initial luminance of 500 cd/m$^2$, the half lifetime was founded to be 20,000 hours or more.

Example 3

The organic EL device was fabricated similarly as Example 1 except that Compound (D-9) was used in place of Compound (D-1). The device was tested by passing electric current, a blue light emission with a current efficiency of 8.6 cd/A and an emission luminance of 860 cd/m$^2$ (maximum light emission wavelength: 471 nm) was observed at a voltage of 6.5 V and a current density of 10 mA/cm$^2$. It was continuously tested by passing electric current at an initial luminance of 500 cd/m$^2$, the half lifetime was founded to be 20,000 hours or more.

Example 4

The organic EL device was fabricated similarly as Example 1 except that 10-(3-(naphthalene-1-yl)phenyl)-9-(naphthalene-2-yl)anthracene in place of BTBAN was used as the host material. The device was tested by passing electric current, a blue light emission with a current efficiency of 8.0 cd/A and an emission luminance of 799 cd/m$^2$ (maximum light emission wavelength: 469 nm) was observed at a voltage of 6.5 V and a current density of 10 mA/cm$^2$. It was continuously tested by passing electric current at an initial luminance of 500 cd/m$^2$, the half lifetime was founded to be 20,000 hours or more.

Example 5

The organic EL device was fabricated similarly as Example 2 except that 1-(9,9-dimethyl-2(pyrene-1-yl)-9-fluorene-7-yl)pyrene in place of BTBAN was used as the host material. The device was tested by passing electric current, a blue light emission with a current efficiency of 7.6 cd/A and an emission luminance of 760 cd/m$^2$ (maximum light emission wavelength: 469 nm) was observed at a voltage of 6.5 V and a current density of 10 mA/cm2. It was continuously tested by passing electric current at an initial luminance of 500 cd/m$^2$, the half lifetime was founded to be 18,000 hours or more.

Example 6

The organic EL device was fabricated similarly as Example 2 except that 1-(4-(naphthalene-1-yl)phenyl)-6-(naphthalene-2-yl)pyrene in place of BTBAN was used as the host material. The device was tested by passing electric current, a blue light emission with a current efficiency of 7.8 cd/A and an emission luminance of 780 cd/m$^2$ (maximum light emission wavelength: 469 nm) was observed at a voltage of 6.5 V and a current density of 10 mA/cm2. It was continuously tested by passing electric current at an initial luminance of 500 cd/m$^2$, the half lifetime was founded to be 19,000 hours or more.

Comparative Example 1

The organic EL device was fabricated similarly as Example 1 except that 6,12-bis(diphenylamino)chrysene in place of Compound (D-1) was used as the doping material. The device was tested by passing electric current, a blue light emission with a current efficiency of 3.1 cd/A and an emission luminance of 311 cd/m$^2$ (maximum light emission wavelength: 451 nm) was observed at a voltage of 6.2 V and a current density of 10 mA/cm$^2$. It was continuously tested by passing electric current at an initial luminance of 500 cd/m$^2$, the short half lifetime was founded to be 1,000 hours.

Comparative Example 2

The organic EL device was fabricated similarly as Example 1 except that 6,12-bis(4-isopropylphenyl-p-tolylamino)chrysene in place of Compound (D-1) was used as the doping material. The device was tested by passing electric current, a blue light emission with a current efficiency of 5.9 cd/A and an emission luminance of 594 cd/m$^2$ (maximum light emission wavelength: 462 nm) was observed at a voltage of 6.3 V and a current density of 10 mA/cm$^2$. It was continuously tested by passing electric current at an initial luminance of 500 cd/m$^2$, the short half lifetime was founded to be 4,590 hours. According to the above results, it was shown that the organic EL devices on Examples 1 to 6 have longer lifetimes than those of the organic EL devices of Comparative Examples 1 and 2 since two or more of substituent bonded to the terminal benzene rings of the doping materials prevent from the association between Compounds in the organic EL devices.

INDUSTRIAL APPLICABILITY

As explained above in details, the organic EL device employing the aromatic amine derivatives of the present invention exhibits adequate luminance of emitted light at low driving voltage and high current efficiency, and has a long lifetime due to its difficult deterioration during a long time use. Therefore, it can be useful for applying it to a flat light emitter of a flat panel display for a television hanging on walls, a backlight for a display and the like.

We claim:
1. An organic electroluminescence device which comprises at least one organic thin film layer comprising a light emitting layer sandwiched between a pair of electrode consisting of an anode and a cathode, wherein at least one of the organic thin film layers comprises an aromatic amine derivative represented by the following general formula (2):

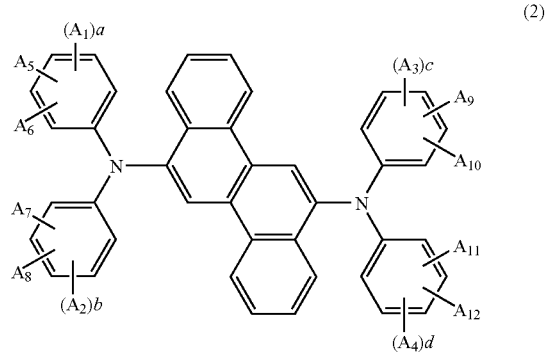

wherein
$A_1$ to $A_4$ each independently represents a hydrogen atom, a substituted or unsubstituted alkyl group having carbon atoms of 1 to 50, a substituted or unsubstituted aryl group having ring carbon atoms of 5 to 50, a substituted or unsubstituted aralkyl group having ring carbon atoms of 6 to 50, a substituted or unsubstituted cycloalkyl group having ring carbon atoms of 3 to 50, a substituted or unsubstituted alkoxyl group having ring carbon atoms of 1 to 50, a substituted or unsubstituted aryloxy group having ring carbon atoms of 5 to 50, a substituted or unsubstituted arylamino group having ring carbon atoms of 5 to 50, a substituted or unsubstituted alkylamino group having carbon atoms of 1 to 20, a substituted or unsubstituted hetero ring group having ring carbon atoms of 5 to 50 or a halogen atom; a, b, c and d each independently represents an integer of 0 or 1; and $A_5$ to $A_{12}$ each independently represents a substituted or unsubstituted alkyl group having carbon atoms of 1 to 50, a substituted or unsubstituted aryl group having ring carbon atoms of 5 to 50, a substituted or unsubstituted aralkyl group having ring carbon atoms of 6 to 50, a substituted or unsubstituted cycloalkyl group having ring carbon atoms of 3 to 50, a substituted or unsubstituted alkoxyl group having ring carbon atoms of 1 to 50, a substituted or unsubstituted aryloxy group having ring carbon atoms of 5 to 50, a substituted or unsubstituted arylamino group having ring carbon atoms of 5 to 50, a substituted or unsubstituted alkylamino group having carbon atoms of 1 to 20, a substituted or unsubstituted hetero ring group having ring carbon atoms of 5 to 50 or a halogen atom; $A_5$ and $A_6$, $A_7$ and $A_8$, $A_9$ and $A_{10}$, and $A_{11}$ and $A_{12}$ may bond each other to form a saturated or unsaturated ring;

provided that the general formula (2) does not include the following compound:

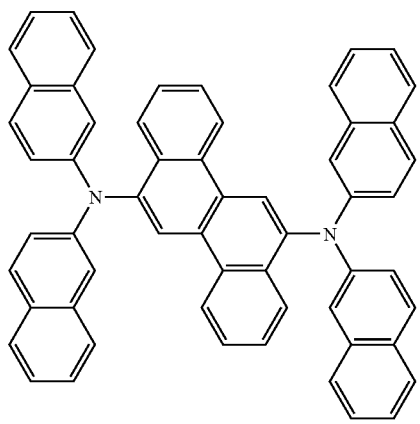

and wherein the light emitting layer comprises the aromatic amine derivative as a doping material and an anthracene derivative represented by the following general formula (3) as a host material:

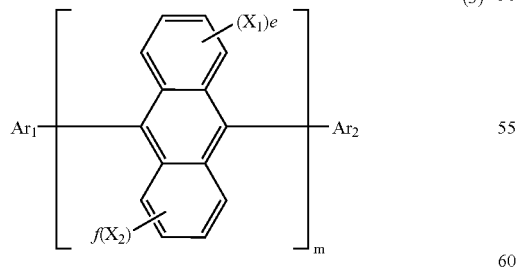

(3)

wherein, $X_1$ and $X_2$ each independently represents a hydrogen atom, a substituted or unsubstituted alkyl group having carbon atoms of 1 to 50, a substituted or unsubstituted aryl group having ring carbon atoms of 5 to 50, a substituted or unsubstituted aralkyl group having ring carbon atoms of 6 to 50, a substituted or unsubstituted cycloalkyl group having ring carbon atoms of 3 to 50, a substituted or unsubstituted alkoxyl group having ring carbon atoms of 1 to 50, a substituted or unsubstituted aryloxy group having ring carbon atoms of 5 to 50, a substituted or unsubstituted arylamino group having ring carbon atoms of 5 to 50, a substituted or unsubstituted alkylamino group having carbon atoms of 1 to 20, a substituted or unsubstituted hetero ring group having ring carbon atoms of 5 to 50 or a halogen atom; e and f each independently represents an integer of 0 to 4;

when e and f are two or more, $X_1$ and $X_2$ are the same with or different from each other;

$Ar_1$ and $Ar_2$ each independently represents a substituted or unsubstituted aryl group having ring carbon atoms of 5 to 50, a substituted or unsubstituted hetero ring group having ring carbon atoms of 5 to 50, and $Ar_1$ and/or $Ar_2$ represents a substituted or unsubstituted aryl group containing a hetero ring having ring carbon atoms of 10 to 50;

m represents an integer of 1 to 3;

when m is 2 or more, the groups in [ ] may be the same with or different from each other.

2. An organic electroluminescence device according to claim 1, wherein $A_5$ to $A_{12}$ each independently represents a substituted or unsubstituted alkyl group having carbon atoms of 1 to 50 in the general formula (2).

3. An organic electroluminescence device according to claim 1, wherein $A_1$ to $A_{12}$ each independently represents a substituted or unsubstituted alkyl group having carbon atoms of 1 to 50 in the general formula (2).

4. An organic electroluminescence device according to claim 1, wherein the aromatic amine derivative is selected from the group consisting of:

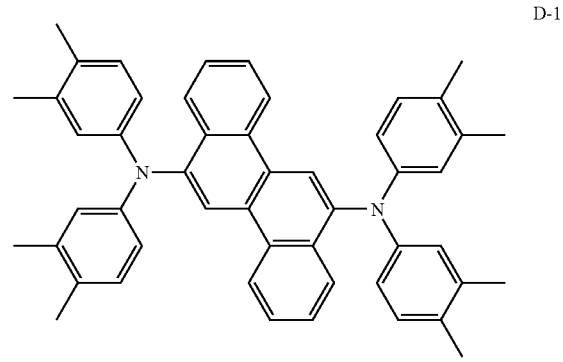

D-1

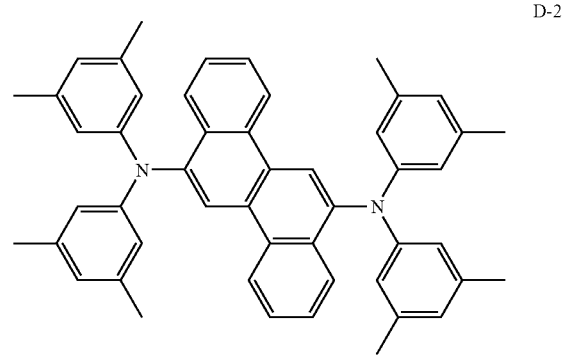

D-2

-continued
D-5
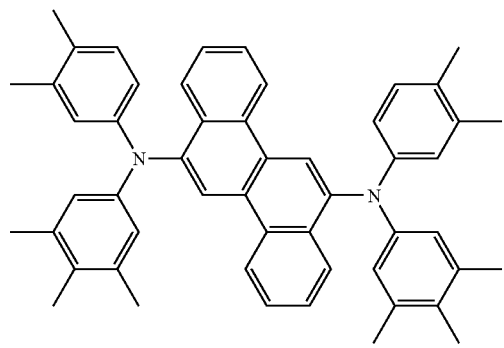
D-6
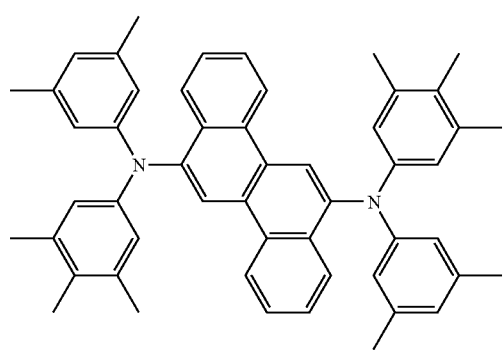
D-9
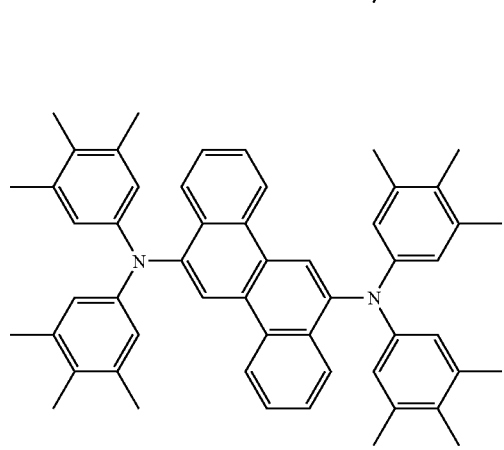
D-17
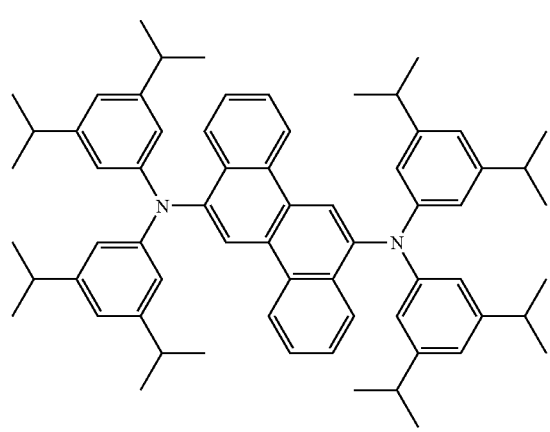
-continued
D-18
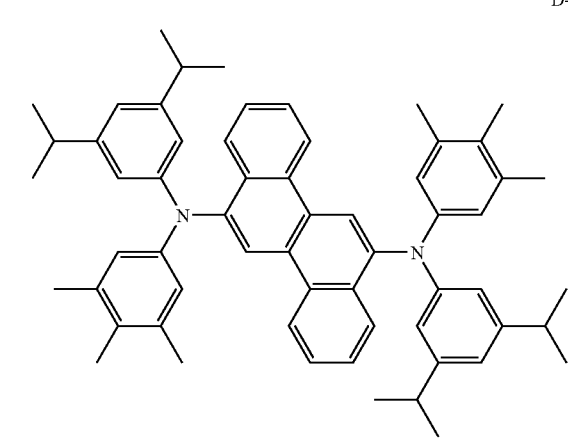
D-20
D-21
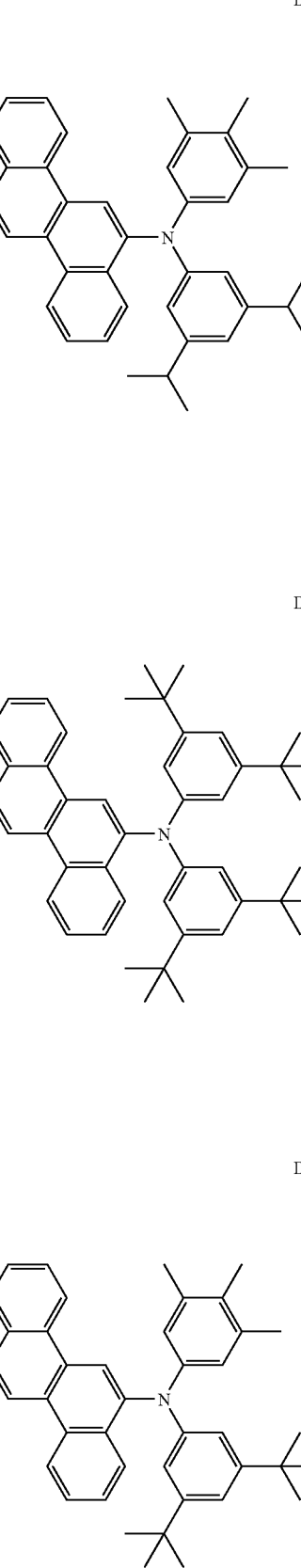

-continued

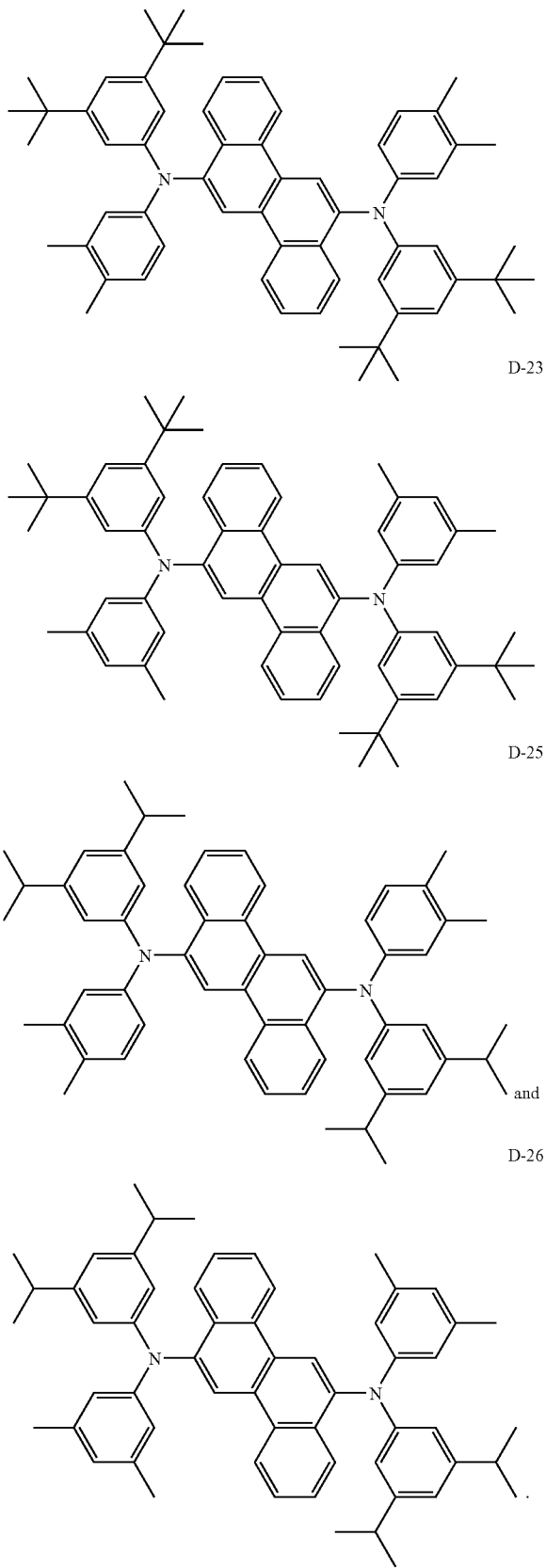

D-22

D-23

D-25 and

D-26

5. The organic electroluminescence device according to claim 1, wherein said light emitting layer comprises 0.1-20 wt. % of the aromatic amine derivative.

6. The organic electroluminescence device according to claim 1, wherein the organic electroluminescence device emits blue light.

7. An organic electroluminescence device which comprises at least one organic thin film layer comprising a light emitting layer sandwiched between a pair of electrode consisting of an anode and a cathode, wherein at least one of the organic thin film layers comprises an aromatic amine derivative represented by the following general formula (2):

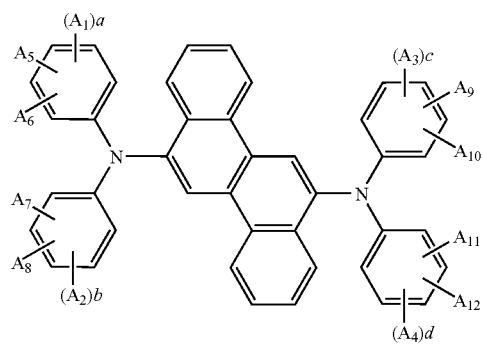

(2)

wherein $A_1$ to $A_4$ each independently represents a hydrogen atom, a substituted or unsubstituted alkyl group having carbon atoms of 1 to 50, a substituted or unsubstituted aryl group having ring carbon atoms of 5 to 50, a substituted or unsubstituted aralkyl group having ring carbon atoms of 6 to 50, a substituted or unsubstituted cycloalkyl group having ring carbon atoms of 3 to 50, a substituted or unsubstituted alkoxyl group having ring carbon atoms of 1 to 50, a substituted or unsubstituted aryloxy group having ring carbon atoms of 5 to 50, a substituted or unsubstituted arylamino group having ring carbon atoms of 5 to 50, a substituted or unsubstituted alkylamino group having carbon atoms of 1 to 20, a substituted or unsubstituted hetero ring group having ring carbon atoms of 5 to 50 or a halogen atom; a, b, c and d each independently represents an integer of 0 or 1; and $A_5$ to $A_{12}$ each independently represents a substituted or unsubstituted alkyl group having carbon atoms of 1 to 50, a substituted or unsubstituted aryl group having ring carbon atoms of 5 to 50, a substituted or unsubstituted aralkyl group having ring carbon atoms of 6 to 50, a substituted or unsubstituted cycloalkyl group having ring carbon atoms of 3 to 50, a substituted or unsubstituted alkoxyl group having ring carbon atoms of 1 to 50, a substituted or unsubstituted aryloxy group having ring carbon atoms of 5 to 50, a substituted or unsubstituted arylamino group having ring carbon atoms of 5 to 50, a substituted or unsubstituted alkylamino group having carbon atoms of 1 to 20, a substituted or unsubstituted hetero ring group having ring carbon atoms of 5 to 50 or a halogen atom; $A_5$ and $A_6$, $A_7$ and $A_8$, $A_9$ and $A_{10}$ and $A_{11}$ and $A_{12}$ may bond each other to form a saturated or unsaturated ring;

provided that the general formula (2) does not include the following compound:

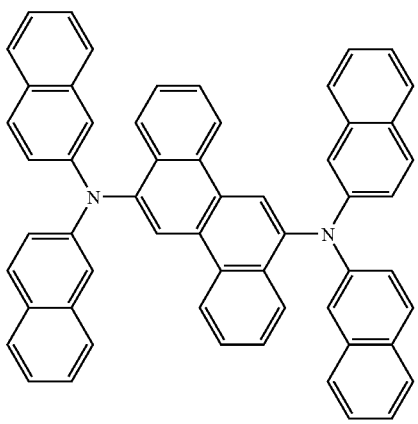

and wherein the light emitting layer comprises the aromatic amine derivative as a doping material and an anthracene derivative represented by the following general formula (4) as a host material:

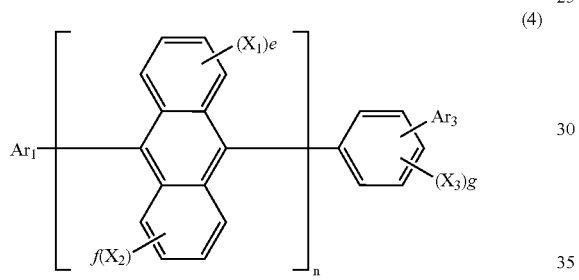

(4)

wherein, $X_1$ to $X_3$ each independently represents a hydrogen atom, a substituted or unsubstituted alkyl group having carbon atoms of 1 to 50, a substituted or unsubstituted aryl group having ring carbon atoms of 5 to 50, a substituted or unsubstituted aralkyl group having ring carbon atoms of 6 to 50, a substituted or unsubstituted cycloalkyl group having ring carbon atoms of 3 to 50, a substituted or unsubstituted alkoxyl group having ring carbon atoms of 1 to 50, a substituted or unsubstituted aryloxy group having ring carbon atoms of 5 to 50, a substituted or unsubstituted arylamino group having ring carbon atoms of 5 to 50, a substituted or unsubstituted alkylamino group having carbon atoms of 1 to 20, a substituted or unsubstituted hetero ring group having ring carbon atoms of 5 to 50 or a halogen atom; e, f and g each independently represents an integer of 0 to 4;

when e, f and g are two or more, $X_1$, $X_2$ and $X_3$ are the same with or different from each other;

$Ar_1$ represents a substituted or unsubstituted aryl group containing a condensed hetero ring having ring carbon atoms of 10 to 50, and $Ar_3$ represents a substituted or unsubstituted aryl group having ring carbon atoms of 5 to 50;

n represents an integer of 1 to 3;

when n is 2 or more, the groups in [ ] may be the same with or different from each other.

8. An organic electroluminescence device according to claim 7, wherein $A_5$ to $A_{12}$ each independently represents a substituted or unsubstituted alkyl group having carbon atoms of 1 to 50 in the general formula (2).

9. An organic electroluminescence device according to claim 7, wherein $A_1$ to $A_{12}$ each independently represents a substituted or unsubstituted alkyl group having carbon atoms of 1 to 50 in the general formula (2).

10. An organic electroluminescence device according to claim 7, wherein the aromatic amine derivative is selected from the group consisting of:

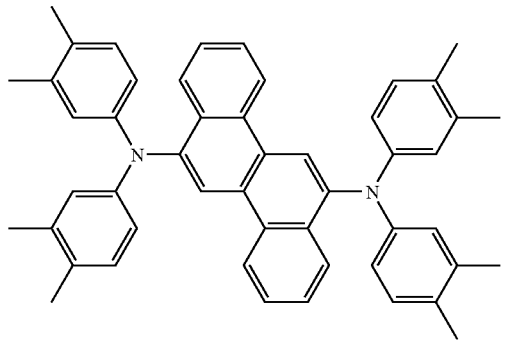

D-1

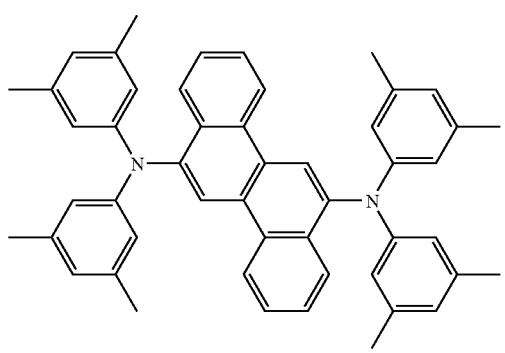

D-2

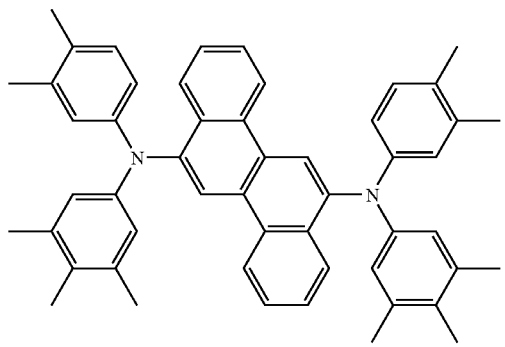

D-5

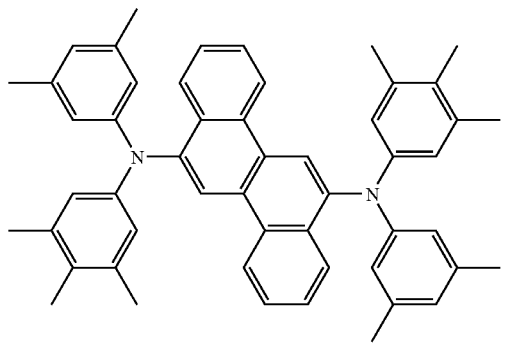

D-6

-continued
D-9
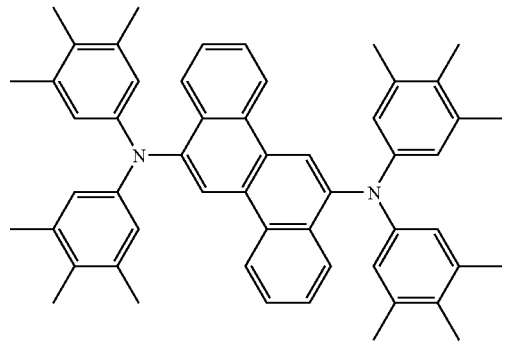
D-17
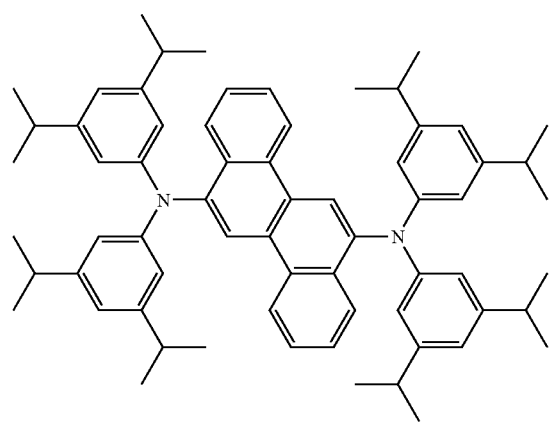
D-18
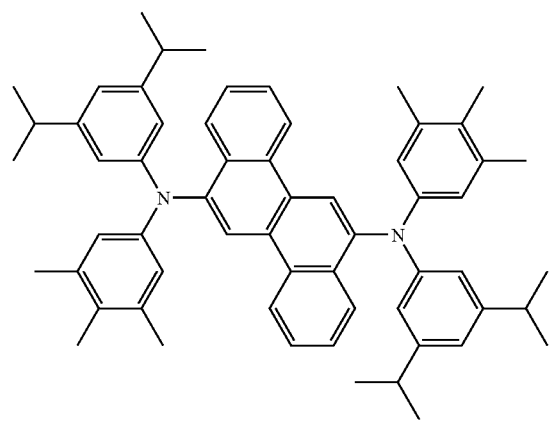
D-20
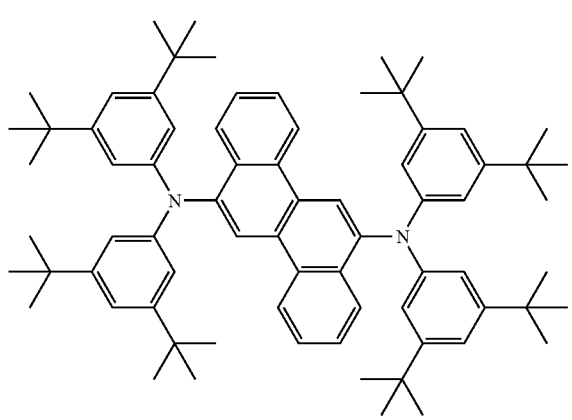
-continued
D-21
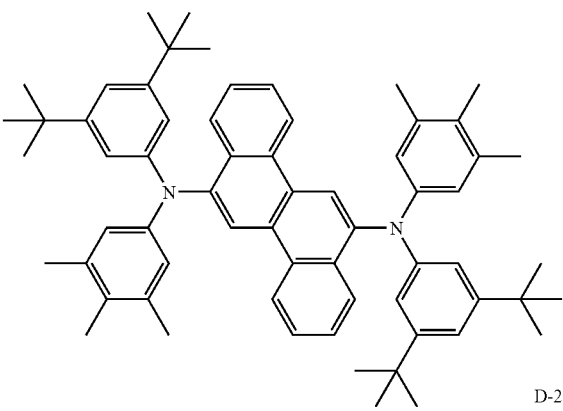
D-22
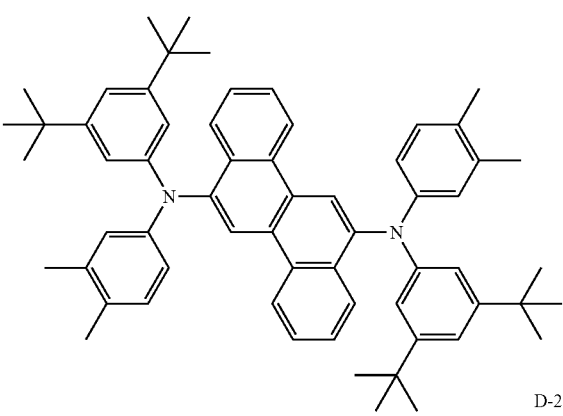
D-23
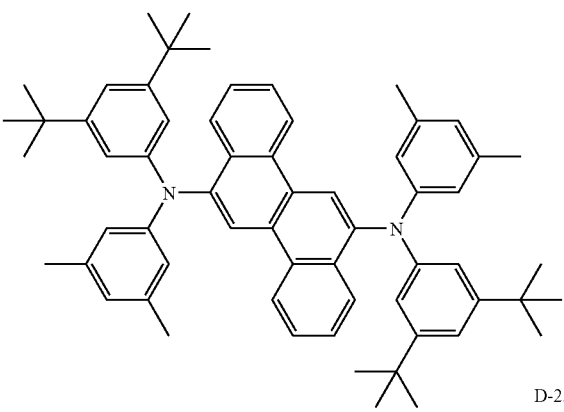
D-25
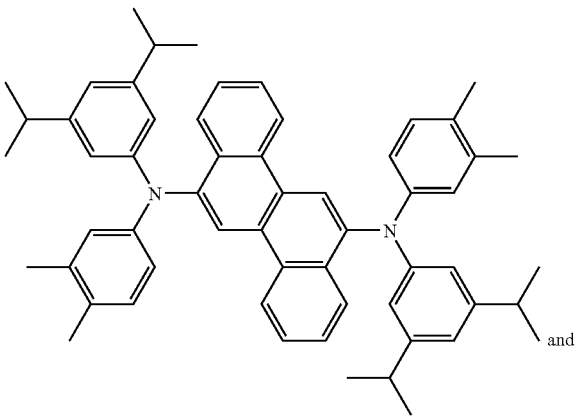
and -continued

D-26

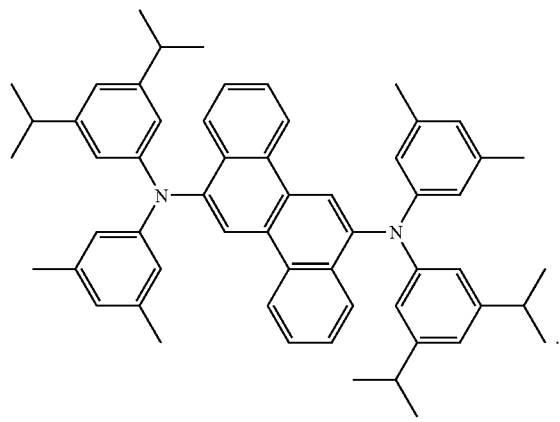

11. The organic electroluminescence device according to claim 7, wherein said light emitting layer comprises 0.1-20 wt. % of the aromatic amine derivative.

12. The organic electroluminescence device according to claim 7, wherein the organic electroluminescence device emits blue light.

13. The organic electroluminescence device according to claim 7, wherein said light emitting layer comprises 0.1-20 wt. % of the aromatic amine derivative.

14. The organic electroluminescence device according to claim 7, wherein the organic electroluminescence device emits blue light.

15. An organic electroluminescence device which comprises at least one organic thin film layer comprising a light emitting layer sandwiched between a pair of electrode consisting of an anode and a cathode, wherein at least one of the organic thin film layers comprises an aromatic amine derivative represented by the following general formula (2):

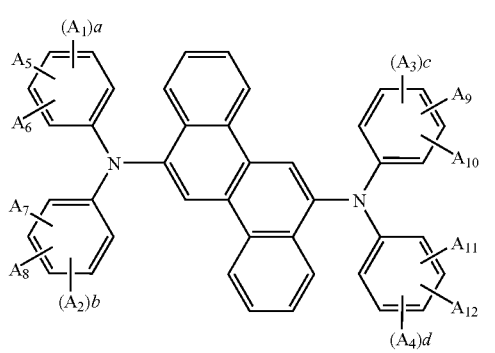

(2)

wherein $A_1$ to $A_4$ each independently represents a hydrogen atom, a substituted or unsubstituted alkyl group having carbon atoms of 1 to 50, a substituted or unsubstituted aryl group having ring carbon atoms of 5 to 50, a substituted or unsubstituted aralkyl group having ring carbon atoms of 6 to 50, a substituted or unsubstituted cycloalkyl group having ring carbon atoms of 3 to 50, a substituted or unsubstituted alkoxyl group having ring carbon atoms of 1 to 50, a substituted or unsubstituted aryloxy group having ring carbon atoms of 5 to 50, a substituted or unsubstituted arylamino group having ring carbon atoms of 5 to 50, a substituted or unsubstituted alkylamino group having carbon atoms of 1 to 20, a substituted or unsubstituted hetero ring group having ring carbon atoms of 5 to 50 or a halogen atom; a, b, c and d each independently represents an integer of 0 or 1; and $A_5$ to $A_{12}$ each independently represents a substituted or unsubstituted alkyl group having carbon atoms of 1 to 50, a substituted or unsubstituted aryl group having ring carbon atoms of 5 to 50, a substituted or unsubstituted aralkyl group having ring carbon atoms of 6 to 50, a substituted or unsubstituted cycloalkyl group having ring carbon atoms of 3 to 50, a substituted or unsubstituted alkoxyl group having ring carbon atoms of 1 to 50, a substituted or unsubstituted aryloxy group having ring carbon atoms of 5 to 50, a substituted or unsubstituted arylamino group having ring carbon atoms of 5 to 50, a substituted or unsubstituted alkylamino group having carbon atoms of 1 to 20, a substituted or unsubstituted hetero ring group having ring carbon atoms of 5 to 50 or a halogen atom; $A_5$ and $A_6$, $A_7$ and $A_8$, $A_9$ and $A_{10}$, and $A_{11}$ and $A_{12}$ may bond each other to form a saturated or unsaturated ring;

provided that the general formula (2) does not include the following compound:

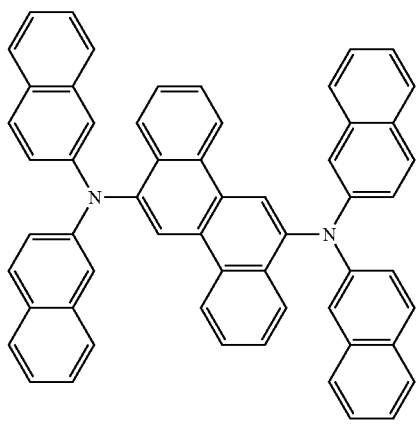

and wherein the light emitting layer comprises the aromatic amine derivative as a doping material and a pyrene derivative represented by the following general formula (5) as a host material:

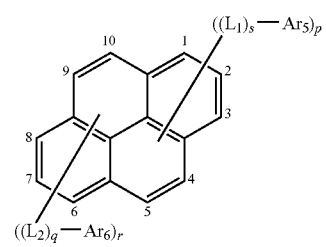

(5)

wherein, $Ar_5$ and $Ar_6$ each independently represents a substituted or unsubstituted aryl group having ring carbon atoms of 6 to 50;

$L_1$ and $L_2$ each independently represents a substituted or unsubstituted phenylene group, a substituted or unsubstituted naphthalenylene group, a substituted or unsubstituted fluorenylene group or a substituted or unsubstituted dibenzosilolylene group;

s represents an integer of 0 to 2, p represents of an integer of 1 to 4, q represents an integer of 0 to 2 and r represents an integer of 0 to 4;

$L_1$ or $Ar_5$ bonds to any one of 1 to 5 positions of pyrene, and $L_2$ or $Ar_6$ bonds to any one of 6 to 10 position thereof;

however, when p+r is an even number, $Ar_5$, $Ar_6$, $L_1$ and $L_2$ satisfy a following requirement (1) or a requirement (2):

(1) $Ar_5 \neq Ar_6$ and/or $L_1 \neq L_2$, wherein ≠ means that each group has a different structure, (2) when $Ar_5 = Ar_6$ and $L_1 = L_2$ (2-1) s≠q and/or p≠r, or (2-2) when s=q and p=r, (2-2-1) both $L_1$ and $L_2$ or pyrene bond respectively to a different position of $Ar_5$ and $Ar_6$, or (2-2-2) both $L_1$ and $L_2$ or pyrene bond respectively to the same position of $Ar_5$ and $Ar_6$ excluding a case where both $L_1$ and $L_2$ or both $Ar_5$ and $Ar_6$ bond respectively to 1 and 6, or 2 and 7 positions thereof.

16. An organic electroluminescence device according to claim 15, wherein $A_5$ to $A_{12}$ each independently represents a substituted or unsubstituted alkyl group having carbon atoms of 1 to 50 in the general formula (2).

17. An organic electroluminescence device according to claim 15, wherein $A_1$ to $A_{12}$ each independently represents a substituted or unsubstituted alkyl group having carbon atoms of 1 to 50 in the general formula (2).

18. An organic electroluminescence device according to claim 15, wherein the aromatic amine derivative is selected from the group consisting of:

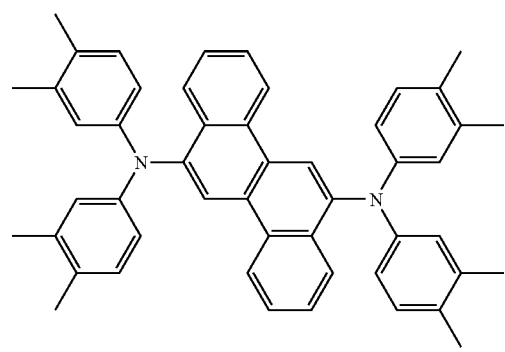
D-1

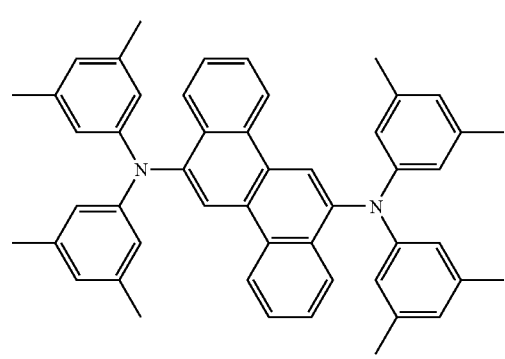
D-2

-continued

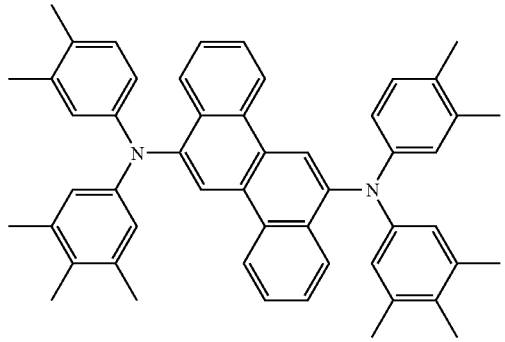
D-5

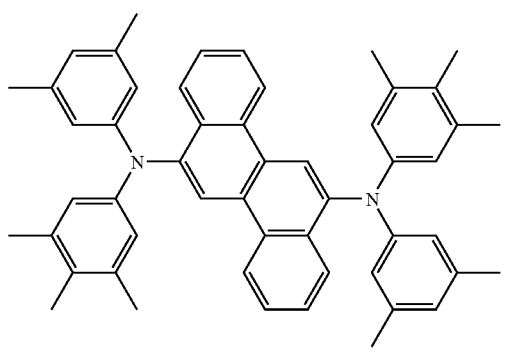
D-6

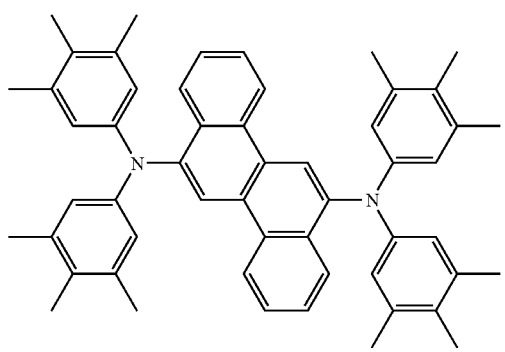
D-9

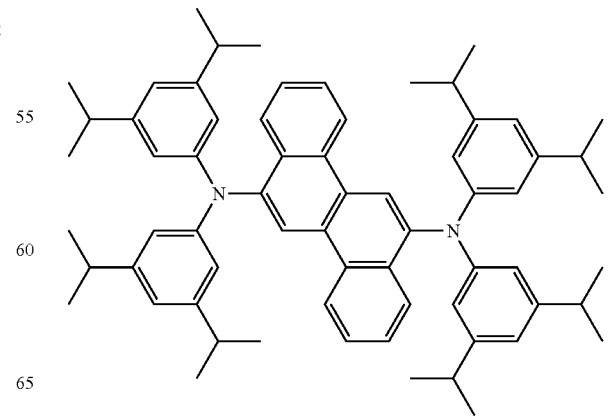
D-17

D-18
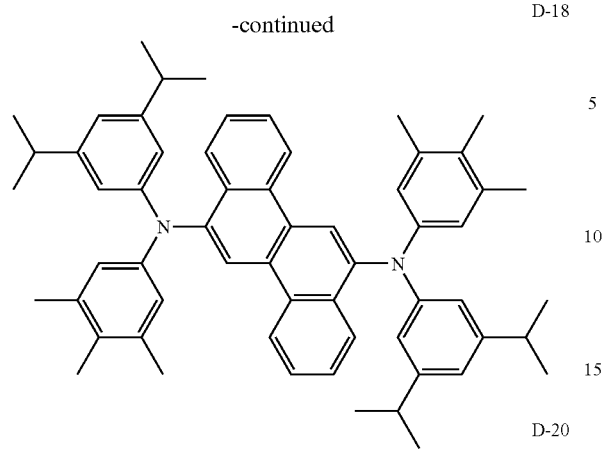
D-23
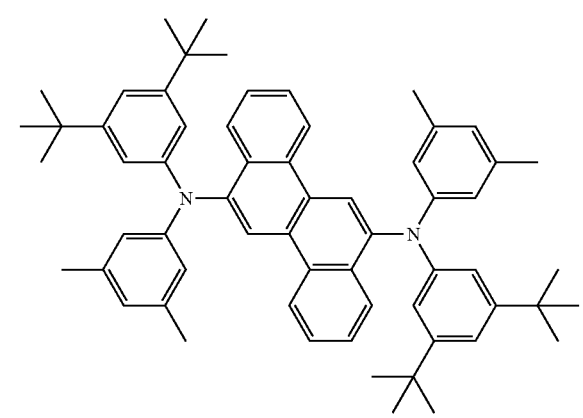
D-20
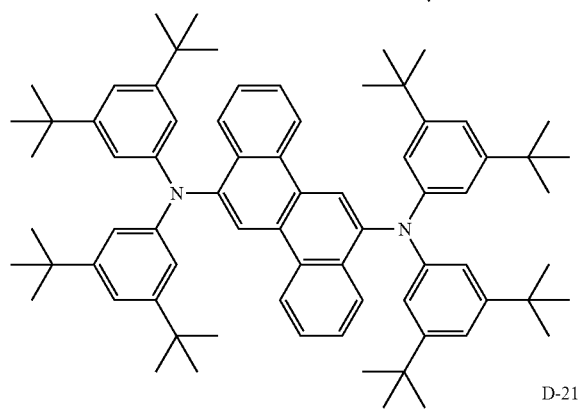
D-25
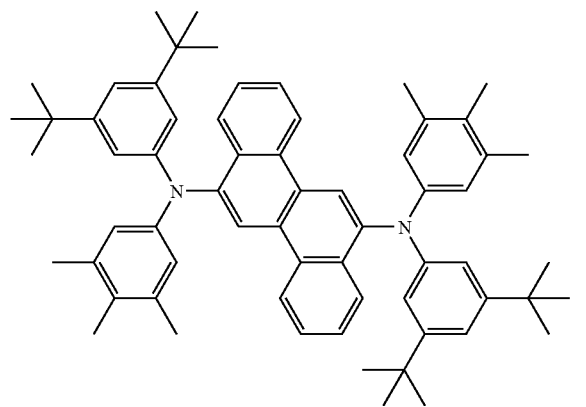
and
D-21
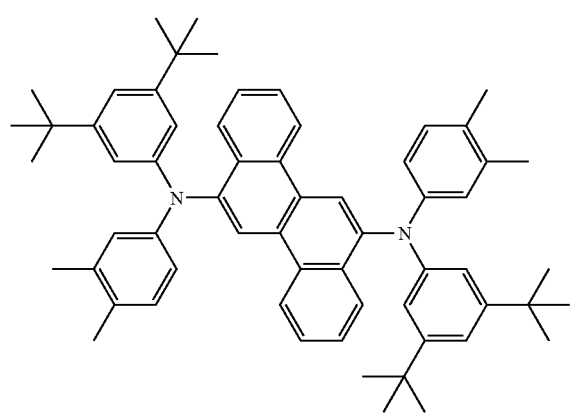
D-26
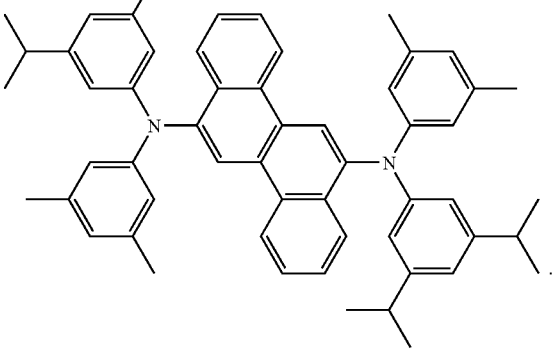
.
D-22
* * * * *